United States Patent [19]

Paradies

[11] Patent Number: 5,248,815
[45] Date of Patent: Sep. 28, 1993

[54] STEREO-SELECTIVE SYNTHESIS OF 2-ARYL-PROPIONIC ACIDS OF HIGH OPTICAL PURITY BY USING CHIRAL OXAZOLINES

[76] Inventor: Henrich H. Paradies, Goerresstr. 38, D-5860 Iserlohn, Fed. Rep. of Germany

[21] Appl. No.: 815,057

[22] Filed: Dec. 27, 1991

[51] Int. Cl.$^5$ .................. C07C 62/06; C07C 53/134
[52] U.S. Cl. .................. 562/496; 562/466; 562/469; 562/492; 562/490
[58] Field of Search .......... 562/496, 466, 469, 492, 562/490

[56] References Cited

U.S. PATENT DOCUMENTS 4,209,638  6/1980  Nicholson et al. .................. 562/401

FOREIGN PATENT DOCUMENTS 2605650  12/1976  Fed. Rep. of Germany .
7058641  4/1982  Japan .

OTHER PUBLICATIONS

Meyers, et al., Oxazolines. XIV. An Asymmetric Synthesis of R and S Dialkylacetic Acids from a Single Chiral Oxazoline, JACS, 96:20, Oct. 2, 1974, pp. 6508-6510.

Hoobler, et al., Origins of Steroselectivity in Asymmetric Syntheses Using Chiral Oxazolines, JACS, 100:26, Dec. 20, 1978, pp. 8182-8185.

Teulon, et al., Antiinflammatory and Analgesic Diastereoisomeric Derivatives of Indan-5-acetic Acid, Journal of Medicinal Chemistry, 1978, vol. 21, No. 9, pp. 901-905.

Yamaguchi, et al., Asymmetric Reductions with Chiral Reagents from Lithium Aluminum Hydride and (+)-(2S,3R)-4-Dimethylamino-3-methyl-1,2-diphenyl-2-butanol, J. Org. Chem., vol. 38, No. 10, (1973), pp. 1870-1877.

Yamaguchi, et al., A Reversal in Stereoselectivity Depending upon the Age of a Chiral Lithium Alkoxyaluminohydride Reducing Agent, JACS, 94:26, Dec. 27, 1972, pp. 9254-9255.

Hayashi, et al., Chiral (Beta-Aminoalkyl)phosphines, Highly efficient Phosphine Ligands for Catalytic Asmmetric Grignard Cross-Coupling, J. Org. Chem. 1983, 48, pp. 2195-2202.

Meyers, et al., The Synthetic Utility of 2-Oxazolines, Agnew. Chem. Int. Ed. Engl., vol. 15, (1976) No. 5, pp. 270-280.

Meyers, et al., Synthesis via 2-Oxazolines. IV. An Asymmetric Synthesis of 2-Methylalkanoic Acids from a Chiral Oxazoline, JACS, 95:1, Jan. 9, 1974, pp. 268-270.

Meyers, et al., Asymmetric Synthesis of R and S alpha-Alkylalkanoic Acids from Metalation and Alkylation of Chiral 2-Oxazolines, JACS, 98:2, Jan. 21, 1976, pp. 567-576.

Meyers, et al., Oxazolines. IX. Synthesis of Homologated Acetic Acids & Esters, J. Org. Chem., vol. 39, No. 18, 1974, pp. 2778-2783.

Kobler, et al., Synthese von Nitrilen mit Tetraalklammoniumcyaniden, Liebigs Ann. Chem., 1978, 1946-1962.

*Primary Examiner*—Paul J. Killos
*Attorney, Agent, or Firm*—Scully, Scott, Murphy & Presser

[57] ABSTRACT

The present invention relates to a stereospecific chemical synthesis of optically pure enantiomers of 2-arylalkanoic acids, especially those of the biologically active (S)-aryl-propionic acids, in good chemical yields, useful for preparing large quantities thereof, and having a high optical purity.

42 Claims, No Drawings

STEREO-SELECTIVE SYNTHESIS OF 2-ARYL-PROPIONIC ACIDS OF HIGH OPTICAL PURITY BY USING CHIRAL OXAZOLINES

FIELD OF THE INVENTION

The present invention relates to a stereospecific chemical synthesis of optically pure enantiomers of 2-aryl-alkanoic acids, especially those of the biologically active (S)-aryl-propionic acids, in good chemical yields, useful for preparing large quantities thereof, and having a high optical purity in the presence of molecular sieves (4.0 Å). The starting material is a suitable substituted (4S,5S)-2-alkyl-4-alkoxy-5-phenyl-2-oxazoline obtained from the corresponding trialkyl orthoalkonates and (1S,2S)-(+)-2-amino-1-phenyl-1,3-diol. The subsequent chemical steps involve reactions with a strong lithium containing base, such as lithium diisopropylamide; and aryl-halide with succeeding protonation yielding large quantities of the corresponding S-enantiomers with high optical purity (>95%). The chiral aminoalcohol can be re-used, as well as the molecular sieves with ease of separation and retention of high optical purity or inexpensive catalytic activities, respectively.

BRIEF SUMMARY OF THE INVENTION

The present invention relates to a stereospecific synthesis, a process applicable to large scale production, for preparing optically active 2-aryl-alkanoic acids, especially 2-aryl-propionic acids in high chemical yields and 95% optical purity as determined by rotation and NMR-techniques. The stereospecific synthesis makes use of suitable substituted (4S,5S)-2-alkyl-4-alkoxy-5-phenyl-2-oxazolines which can be easily obtained by reaction of the corresponding trialkyl orthoalkonates and (1S,2S)-(+)-2-amino-1-phenylpropane-1,3-diol, with subsequent lithiation with lithium containing base such as lithium-diisopropylamide (LDA), followed by arylation through the suitable arylhalide with subsequent protonation. The enantiomeric excess of the S-enantiomer is facilitated by a polar solvents and molecular sieves (4.0 Å) at low temperatures between −20° C. to −35° C.

This chemical process yields high optically pure 2-aryl-propionic acids at high chemical yields with the advantage of re-use of the chiral amino-alcohol as well as the molecular sieves. The R-enantiomer can be obtained through the same route using the (1R,2R)-(−)-2-amino-1-phenylpropane-1,3-diol instead of the (1S,2S)-(+)-antipode.

BACKGROUND OF THE INVENTION

The medicinal aspects of the aryl-acetic acids and their 2-methyl analogues, especially the 2-(R,S)-aryl-propionic acids, have been reviewed by Shen (Shen T. Y., in: Wolff, M. F. (ed), Burger's Medicinal Chemistry, 4th edition, part III, Wiley, Interscience, New York, pp 1205-1271). Numerous clinical studies continue to demonstrate the efficacy of this particular class of compounds against pain and inflammation. It has been shown that some carboxylic acids of this class of compounds process mechanisms of inhibition on the cyclo-oxygenase pathway as well as actions not typical for the cyclo-oxygenase pathway (e.g. see Carty, Th., J., et al. in: Annual Reports in Medicinal Chemistry, Vol. 23, pp 181-189, 1988; Academic Press). For the 2-aryl-propionic acids a stereoselective disposition kinetic has been established, and also an unidirectional metabolic chiral inversion of the less active R-enantiomer to the more active S-isomer (Adams, S., et al., 1976, J. Pharm. Pharmacol. 28, 256; Hutt A. J., and Caldwell, J. Clin. Pharmac., 9, 371, 1984; Hutt, A. J., and Caldwell, J., J. Pharm. Pharmacol., 35, 693, 1983). Moreover, new studies have revealed that intravenous injection of racemic ibuprofen inhibits the neutrophil dependent edema response of rabbit skin to C5a ala-arg in addition to PGE$_2$, an observation suggesting a non-cyclo-oxygenase action of this derivative of the 2-aryl-propionic acid class (M. Ramport and T. J. Williams, Biochem., Pharmakol, 35, 581, 1986).

Although numerous studies continue to demonstrate the efficacy of this class of 2-arylpropionic acids against pain and inflammation, some studies have also shown that some carboxylic acids of non-steroidal anti-inflammatory drugs possess mechanism of action beyond their classical cyclo-oxygenase pathway inhibition. Furthermore, salicylate which is the major metabolite of aspirin has been observed to be effective in blocking rat paw edema induced by platelet activating factor (PAF) which is believed an activity not shared by other non-steroidal anti-inflammatory drugs. (R. S. Cordeiro, P. M. Silva, M. A. Martins, and B. B. Vorgaflig, Prostaglandin, 32, 719, 1985).

Therefore, the pure S-enantiomers seem to be appropriate for a number of reasons for therapeutic use: e.g., i) a reduction in the dose of the biologically active S-enantiomer with respect to the racemate; ii) substance administration is considerably less than in comparison to the (R,S)-racemic mixture; hence less side effects are most likely to be expected, and iii) the drug action is faster since the receptors are enantiospecific having a high intrinsic affinity for these particular enantiomeric compounds.

Therefore, it is desirable to be able to produce the S-enantiomer on an industrial scale in order to produce economically attractive yields of these S-(+)-enantiomers, having a high optical purity (98%) by applying stereospecific chemical synthesis. Apart from obtaining pure enantiomers of 2-aryl-alkanoic acids, especially 2-aryl-propionic acids, using optically active bases (see Blaschke, G., Angew Chem. 92, 14-25, 1980), or through biochemical racemate separation (P. Lesti and P. Piccardi, Eur. Patent. Appln. EP 195,717, 1986; J. S. Nicholson and J. G. Tantum, U.S. Pat. No. 4,209,638, 1980), only a few chemical stereoselective processes have been disclosed. Also enzymes, especially from pig liver, have been used for racemic separation (Marshek, W. J. and Miyano, M., 1973, Biochim. Biophys. Acta 316, 363).

Furthermore, it has been reported by Cambon and Klibanov (B. Cambon and A. M. Klibanov, Appl. Biochem. and Biotechnology, 9, 255-258, 1984) that a lipase-catalyzed production of optically active acids can be prepared via asymmetric hydrolysis of esters. Specifically, it has been found that lipase from Candida cylindracea hydrolyses octyl R(+) but not S-(−)-2-chloropropionate. See also similar methods which are disclosed in the following references:

Marshek, W. J. and Miyano, M. (1973), Biochim. Biophys. Acta 316, 363.

Oritani, T. and Ymashita, K. (1974), Agric. Biol. Chem. 38, 1965.

Yamaguchi, Y., Oritani, T., Tajima, N., Komatsu, A. and Moroe, T. (1976), J. Aqric. Chem. Soc. Japan 50, 475.

McGahren, We. J., Sax, K. J., Kunstmann, M. P. and Ellestad, G. A. (1977), *J. Org. Chem.* 42, 1659.

Mori, K. and Akao, H. (1980), *Tetrahedron* 36, 91.

Iriuchijima, S. and Keiyu, A. (1981), *Agric. Biol. Chem.* 45, 1389.

Kawai, K., Imuta, M. and Ziffer, H. (1981), *Tetrahedron Lett.*, 22, 2527.

Iriuchijima, S. and Kojima, T. (1982), *Agric. Biol. Chem.* 46, 1153.

Lavayre, J., Verrier, J. and Baratti, J. (1982), *Biotechnol. Bioeng.* 24, 2175.

Iriuchijima, S., Keiyu, A. and Kojima, N. (1982), *Agric. Biol. Chem.* 46, 1593.

The usefulness and industrial application of these methods is restricted by the drawback that only a few of the many lipases exhibit stereospecifity in the hydrolysis of esters.

All of these techniques and biotechnological processes suffer from similar drawbacks at the present time. These processes are inefficient since they require large volumes of material for the recovery and racemization of the desired optical stereoisomer for chemical racemate separation and require redistillation of the solvents used. Finally, after the procedure is completed, only low yields of crystalline compounds of high optical purity are obtained from the mother liquors. Thus, the present invention, by eliminating all these unnecessary steps, will result in substantial savings in material costs, manufacturing, labor and equipment.

Methods for synthesizing racemic 2-aryl-alkanoic acids, especially 2-aryl-propionic acids and in particular (R,S)-ibuprofen, are well known and disclosed in several patents and the scientific literature, e.g. Tanonaka, T., et al., DE 3523082 A1, (1986), who uses microorganisms; JP-PSEN 40-7491 (1965); 47-18105, (1972); JP-OS 50-4040, (1975); DE 2404159 (1974); DE 1443429 (1968) by J. S. Nicholson and S. S. Adams; DE 2614306 by Bruzzese, T., et al., (1976); DE 2605650 by Gay, A., (1976); DE 2545154 by Heusser, J., (1976); and DE 2404160 by Kogure, K., et al., (1974).

Surprisingly, only a few methods for a stereospecific chemical synthesis for 2-aryl-alkanoic acids, especially 2-aryl-propionic acids, are known. Piccolo et al. (*J. Org. Chem.* 50, 3945-3946, 1985) describe a stereospecific synthesis by the alkylation of benzene or isobutylbenzene with (S)-methyl-2-(chlorosulfonyl)-oxy or 2-(mesyloxy) propionate in the presence of aluminum chloride yielding (S)-methyl-2-phenyl-propionate in good chemical yield (50-80%) and excellent optical yield of >97% as determined by rotation through inversion of configuration at the attacking carbon atoms. The reaction conditions are very similar as described in some patents (Jpn. Kokai Tokkyo Koho 5808045; *Chem. Abstracts*, 1983, 98; 143138 k; Jpn. Kokai Tokkyo Koho 7979246; *Chem. Abstracts*, 1980, 92, 6253 f) where racemic reagents have been used. Extensions of this type of reactions to other aromatic substrates, e.g. toluene, isobutylbenzene, tetraline, anisole, naphthalene, 2-methoxy-naphthalene are described in Jpn. Kokai Tokkyo Koho 7971932; *Chem. Abstracts* 1979, 91, 20125 b; Jpn. Kokai Tokkyo Koho 78128327; *Chem. Abstracts* 1978, 89, 23975 y; Jpn. Kokai Tokkyo Koho 81145241; *Chem. Abstracts* 1982, 96, 68650 z; Jpn. Kokai Tokkyo Koho 78149945; *Chem. Abstracts* 1979, 90, 168303 h; Jpn. Kokai Tokkyo Koho 7844537; *Chem. Abstracts* 1978, 89, 108693 h; Jpn. Kokai Tokkyo Koho 77131551; *Chem. Abstracts* 1978, 88, 104920 h. In a recent paper Piccolo et al. (*J. Org. Chem.* 52. 10, 1987) describe a synthesis leading to R-(−) ibuprofen, whereas Tsuchihashi et al. (Eur. Pat. Appl. EP 67,698, (1982); *Chem. Abstracts* 98, 178945 y, (1983) report a stereospecific synthesis of the R-(−) ibuprofen-methylester with excellent yields of about 75.0% and high optical purity (>95%) in contrast to Piccolo et al. (*J. Org. Chem.* 32, 10, 1987) having an optical purity of 15% only for the R-(−) ibuprofen. However, the same authors have reported chemical yields of 68% of S (+) ibuprofen having an optical purity of 75-78%, only. Hayashi, et al. (*J. Org. Chem.* 48, 2195, 1983; in: *Asymmetric Reactions and Processes In Chemistry*; eds E. L. Eliel and S. Otsuka, ACS-Symposium Ser. 1985, 1982, 177) describe a stereospecific synthesis of S-(+) ibuprofen through asymmetric Grignard cross-coupling which are catalyzed by chiral phosphine-nickel and phosphine-palladium complexes. The enantiomeric excess of the coupling products with various alkenyl halides under the influence of the above-mentioned metal phosphine complexes, including amino acids, depends strongly on the ligand and ranges up to 94% with enantiomeric excesses in the 60-70% range. A very useful ligand has been found in chiral 2-aminoalkyl phosphines achieving reasonable chemical yields and high optical purity. Furthermore, optically active 2-aryl-alkonates have been synthesized via a Friedel-Crafts synthesis by Sato and Murai (Jpn. Kokai Tokkyo Koho JP 61,210,049 t 86,210,049, 1986) yielding 46% S-(+) ibuprofen. Giordano et al. (EP application 0 158 913, 1985) have reported a process for the preparation of optically active 2-aryl-alkanoic acids and intermediates thereof by halogenation on the aliphatic carbon atom to the ketal group and rearrangements of the haloketals yielding pharmacologically active 2-aryl-alkanoic acids. A stereochemical synthesis of 2-aryl-propionic acids is described by Robertson et al. (EP application 0 205 215 A2, 1986) using 2-($R_1$)-alkane as the carbon source for the fungi Cordiceps in particular for *Cordiceps militaris*, yielding enantiomeric S-(+) products of high optical purity.

Methods for the synthesis of anti-inflammatory 2-aryl-propionic acids are listed in the review by Rieu et al. (J. P. Rieu, A. Boucherle, H. Coussee and G. Mouzin, *Tetrahedron Report* No. 205, 4095-4131, 1986), also. However, this report is mostly concerned with the racemates rather than an evaluation of stereospecific chemical synthesis of 2-aryl-propionic acids.

In addition a new report on the stereochemical synthesis of 2-aryl-propionic acids for pure S- or R-enantiomers is disclosed in Kontakte (Darmstadt, 3, 13-15, 1989) as well as in a very recent paper by Lassen et al. (R. D. Lassen, E. G. Corley, P. Davis, P. J. Reider and E. J. J. Grabowski, *J. Amer. Chem. Soc.* 111, 7650, 1989)

The advances in catalytic asymmetric reactions applying transition metal complexes, i.e., the direct conversion of 1-aryl-ethane-halides of the R or S conformation with sodium tetracarboxyl-ferrate (-II) ($Na_2Fe(CO)_4$) in the presence of triphenylphosphine ($Ph_3P$), has made it possible to synthesize chiral compounds with high enantiomer excess and economical good yields (for review see, i.e., Ojima, I., Llos., N., Barton, C., Tetrahedron 1989, 45, 6091). Very recently it was possible to demonstrate that stoichiometric amounts of certain chiral materials can be very effectively applied as chiral materials in the presence of molecular sieves to obtain the desired chiral compound from a prochiral unsymmetrical ketone.

The present invention relates to a process of preparing a compound is stereospecific form of the formula:

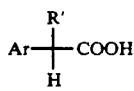

or pharmaceutically acceptable salts thereof wherein
Ar is a monocyclic, polycyclic or orthocondensed polycyclic aromatic group having up to 12 carbons in the aromatic ring which may be substituted or unsubstituted in the aromatic ring which comprises (a) reacting (4S,5S)-2-alkyl-4-alkoxy-5-phenyloxazoline with a Group I metal containing base wherein the phenyloxazoline has the formula

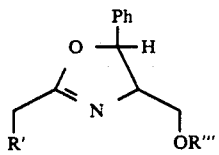

wherein
R' is lower alkyl;
R''' is alkyl containing 1-10 carbon atoms;
Ph is phenyl or phenyl substituted with lower alkyl (b) reacting the product of (a) with Ar-Hal, wherein Ar is as defined hereinabove and Hal is halide.

DETAILED DESCRIPTION OF THE INVENTION

Some uses of chiral oxazolines have been summarized by Meyers and Mihelich, (A. I. Meyers and E. D. Mihelich, *Angew. Chem.* 88 321, 1976; A. I. Meyers, D. L. Temple, R. L. Nolen and E. D. Mihelich, *J. Org. Chem.* 39, 2778, 1974; A. I. Meyers, G. Knauss, K. Kamata, and M. E. Ford, *J. Amer. Chem. Soc.* 98, 567, 1976). Furthermore the use of chiral oxazolines as auxiliaries in asymmetric carbon-carbon bond forming reactions for 2,3-disubstituted carboxylic acids, aldol products through boron enolates of oxazolines as well as enantiomers of α-hydroxy acids as synthons has been reviewed by A. I. Meyers, also, very recently (A. I. Meyers: "Asymmetric Carbon-Carbon Bond-forming Reactions Via Chiral Oxazolines," in *Asymmetric Reactions and Processes in Chemistry*, eds E. L. Eliel, S. Otsuka, ACS-Symposium Series 185, 1982). Reports on stereospecific chemical synthesis for 2-alkyl-alkanoic acids have appeared by A. J. Meyers, G. Knauss and K. Kannata, *J. Amer. Chem. Soc.*, 96, 268, 1974; A. J. Meyers and G. Knauss, *J. Amer. Chem. Soc.* 96, 6508, (1974).

So far the potential ability of chiral oxazolines as a synthon for producing large quantities of S or R-enantiomeric 2-arylpropionic acids of high optical purity of at least 95% enantiomeric excess (ee) has not been disclosed. This particular process of applying chiral oxazolines for producing enantiomeric pure 2-aryl-propionic acids as disclosed in this invention is attractive with respect to industrial large production processes: low costs of the raw materials, the economically inexpensive (1S,2S)-(+)-2-amino-1-phenyl-propane-1,3-diol, which can be reused after completion of the reaction, no purification of the chiral amino-alcohol after acid hydrolysis (see e.g., Scheme I), application of different chiral reduction reagents, e.g. 2,2'-dihydroxy-1,1'-binaphthyl in the presence of a hydroxylic compound R'OH, complexed to oxazolines, in the presence of aryl-methyl-ketones

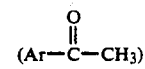

for producing enantiomeric pure secondary alcohols; start reaction times in the reactor due to the presence of molecular sieves, which can be recovered and used again in the process; and low volumes of solvents. Furthermore, most importantly, once the process has been established the whole production can be conducted in one reactor, so a multipurpose plant is not necessary. Furthermore, in contrast to known procedures, applying oxazolines for asymmetric synthesis enables the reaction to be carried out at rates faster than those of the normal stoichiometric system giving products of high enantiomeric selectivity (95-98% ee).

This proposed asymmetric synthesis of 2-aryl-alkanoic acids, especially of the 2-aryl-propionic acids with relation to the (S)-(+)-enantiomers, does not have the cumbersome recovery step for recycling the auxiliary since the chiral reducing or complexed compound, the inexpensive (1S,2S)-(+)-2-amino-1-phenyl-1,3-diol, is obtained as a by-product in addition to the free 2-aryl-alkanoic acid without loss of optical purity. Therefore, one important simplification of this process is the avoidance of any separation, purification from other reaction products without loss of any optical purity accordingly.

As used herein, the term lower alkyl, when used alone or in combination is an alkyl containing 1-6 carbon atoms. The alkyl group may be straight-chained or branched and includes such groups as methyl, ethyl, propyl isopropyl, n-butyl, isobutyl, sec-butyl, tert-butyl, pentyl, amyl, neopentyl, hexyl and the like. It is preferred that the alkyl group contains 1-4 carbon atoms.

The Ar groups are monocyclic, polycyclic or orthocondensed polycyclic aromatic groups having up to 14 ring carbon atoms and up to a total of 18 carbon atoms. The Ar groups may monocyclic, bicyclic or polycyclic and may be unsubstituted or substituted with such groups as lower alkyl, aryl, lower arylalkyl, hydroxy, lower alkoxy, or halo. It is preferred that the Ar groups contain 6-10 ring carbon atoms. Examples of Ar include such groups as phenyl, α-naphthyl, β-naphthyl, and anthryl. The preferred Ar groups are phenyl, 4-isobutylphenyl, 6-methoxy, 2-naphthyl, 3-phenoxyphenyl, 2'fluoro-4-diphenyl, 4'fluoro-4-diphenyl, 5-chloro-6-methoxy-2-naphthyl, 5-bromo-6-methoxy-2-naphthyl, 4-chloro phenyl, 4-difluoro methoxy phenyl, 6-hydroxy-2-naphthyl, or 5-bromo-6-hydroxy-2-naphthyl.

The preferred Ph group is tolyl, phenethyl and especially phenyl.

As defined herein, R' is lower alkyl. It is preferred that R' contains 1-4 carbon atoms. It is especially preferred that R' is methyl, eLhyl, n-butyl and isobutyl.

R''' as used herein is an alkyl group containing 1-10 carbon atoms. This alkyl group may be straight-chained or branched and includes such groups as methyl, ethyl, propyl, isopropyl, n-butyl, isobutyl, sec-butyl, tert-butyl, pentyl, hexyl, amyl, neopentyl, heptyl, octyl, nonyl, decyl and the like. It is preferred that the alkyl group contains 1-8 carbon atoms. It is especially preferred that R''' is methyl, ethyl, n-butyl, isobutyl or n-octyl. It is most preferred that R''' is a bulky lower alkyl group and contains 4 or greater carbon atoms, e.g. isobutyl or octyl. Further, it is preferred that R''' be straight chained.

The term halide refers to fluoride, bromide, chloride or iodide. The preferred halide is chloride or bromide.

A Group I metal is an alkali metal. Preferred examples of Group I metal include sodium, potassium and especially lithium.

A Group I metal containing base is a Group I metal salt of a base, as defined in the Bronsted-Lowry sense. It is preferred that the conjugate acid of said base has a pKa greater than or equal to 15. Examples of Group I containing bases include lithium lower alkyl amide (e.g., lithium, isopropyl amide), lithium lower alkoxide (such as lithium methoxide), lithium acetylide, lithium hydride, lithium hydroxide, lithium triarylmethide (e.g. lithium triphenylmethide), and the like. It is preferred that the pKa of the conjugate acid of the base be greater than or equal to 17. The preferred lithium base is lithium dilower alkyl amide (e.g. lithium diisopropyl amide).

A representative example of the present process is depicted in scheme I; wherein Ph, R', R''', Ar are as defined hereinabove.

The process of the present invention utilizes 2-alkyl-4-alkoxy-5-phenyl oxazolines as defined herein. It is preferred that the oxazoline is chiral, especially since the final product would be in a particular stereospecific form (either R or S at the chiral center).

The 2-alkyl-4-alkoxy-5-phenyl oxazoline is reacted with a Group I metal containing base, such as a lithium containing base, in a solvent. The solvent can be non-polar, weakly polar, polar or polar protic, as described hereinbelow. It is preferred that the solvent is weakly polar, with the most preferred solvent being THF. It is also preferred that the solvent be dried and that the reaction is run under anhydrous conditions and in the absence of air, such as under nitrogen or argon. The reaction can be run at effective temperatures, but it is preferred that the reaction is run at temperatures ranging from room temperature to −90° C. It is especially preferred that the reaction temperature ranges from −75° C. to −10° C. It is preferred that the reaction be run in the presence of a drying agent, such as molecular sieves. It is preferred that molecular sieves 2 Å–8 Å be used with the especially preferred being molecular sieve of 3–5 Å and the most preferred being molecular sieves of 4–5 Å, especially 4 Å. The product formed from this step is depicted as II in Scheme 1.

II is next reacted with an aryl halide as defined herein to produce the 2-aryl-propionic acid of the present invention. The reaction can be run in a solvent, which can be non-polar, weakly polar, polar or polar protic as defined hereinbelow. It is preferred that the solvent is non polar or weakly polar. The most preferred solvent is $CH_2Cl_2$ or THF. The reaction is run at effective temperatures. It is preferred that the reaction is run at temperatures ranging from 40° to −40° C., with the preferred temperature ranging from −25° C. to +25° C. It is preferred that the reaction be run in the presence of a drying agent, such as magnesium sulfate, sodium sulfate or molecular sieves of 2 Å–8 Å, with the most preferred molecular sieves being molecular sieves of 3–5 Å and especially 4 Å. Additionally, it is preferred that the reaction be run in the presence of a strong acid, such as hydrochloric acid, sulfuric acid, nitric acid and the like.

A by product of the present invention is a stereoisomer of 2-amino-1-phenylpropane-1,3-diol of the formula

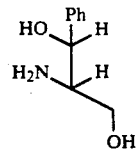

wherein Ph is as defined hereinabove.

However, the compound of Formula III can be used to prepare the oxazoline of Formula I. More specifically, as shown in Scheme I, the oxazoline of Formula I is prepared by reacting the diol of Formula III with a lower trialkyl orthoalkanoate of Formula IV in the presence of R'''X wherein R''' is as defined hereinabove and X is a leaving group, such as halide, R'' is lower alkyl and R is as defined hereinabove. The reaction can be run in a solvent which is slightly polar or polar, as defined hereinbelow. A preferred solvent is methylene chloride, 1, 2-dichloroethane and the like. The reaction can be effected at temperatures ranging from room temperature to the boiling point of the solvent.

SCHEME I
ROUTE FOR THE STEREOCHEMICAL
SYNTHESIS OF 2-(S)-ARYL-ALKANOIC ACIDS

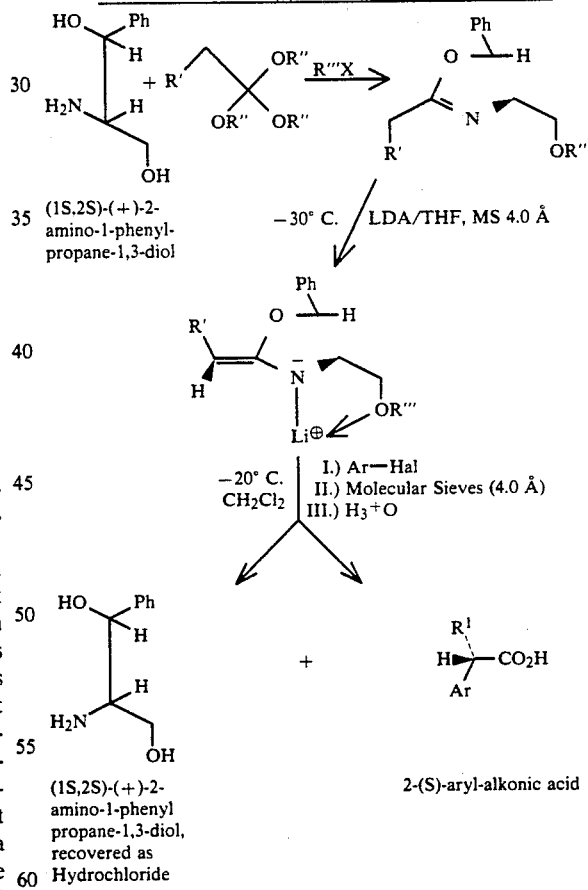

The solvents that can be used in the present invention can be classified into four types:
  non-polar, no ability to solvate cations or anions, e.g. alkanes, benzenes, $CH_2Cl_2$, $CHCl_3$;
  weakly polar, can solvate cations, e.g. ether, THF, DME, di-tri, -tetra-glymes, pyridine, aliphatic tertiary amine;

polar aprotic solvents, having good cation solvating capabilities, however with no ability to directly solvate anions, e.g. hexamethyl phosphoric triamide (HMPT), DMSO, DMF, Me$_2$CO, CH$_3$CN polar protic solvents which can be solvate both anions (hydrogen bonding) and cations, e.g. H$_2$O, NH$_3$, CH$_3$OH, C$_2$H$_2$OH It has been discovered that (i) the solvents used, (ii) the molecular sieves, (iii) and the temperature and (iv) stirring in the presence of the molecular sieves improve the chemical yields (>75%) and provide final products with high optical purity (>95%). Without wishing to be bound, it appears that molecular sieves, when used, improve the optical yield of the stereoselective reaction, especially in CH$_2$Cl$_2$, n-hexane, toluene and benzene. For example, in the case of S-(+)-2-[4-isobutyl-phenyl]-propionic acid, or the S-(+)-2-[6-methoxynaphthyl]propionic acid derivatives, the catalytic reaction according to Scheme (I) with respect to coupling with the Ar-Hal provide products of only 55–60% enantiomeric excess, when the molecular sieves are absent, as compared with 90% ee in their presence (see Table I).

Apparently the molecular sieves facilitate ligand substitution by Ar-Hal, especially for Hal=Br, Cl to the S-form and also helps to optimize with the apolar solvents, e.g., CH$_2$Cl$_2$, toluene or benzene, the stereo-differentiating ability of the lithio-transition complex:

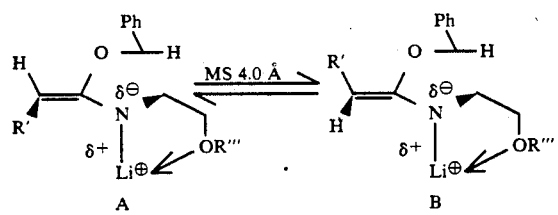

The alkoxy group on the oxazoline appears important. The preferred alkoxy group is the n-butyloxy group. As shown hereinabove, there appears to be an equilibrium between derivatives A and B. Very recent NMR-results indicate that the equilibrium is shifted towards the transconfiguration (B) in the presence of 4.0 Å molecular sieves avoiding the unfavorable cisoid interaction observed in A. B is also considered to be the more stable one, especially in the presence of the molecular sieves of 4.0 Å. Furthermore, applying molecular sieves of the type of ZSM (6–8.0 Å) the chemical yields can reduce considerably from 85% in the presence of 4.0 Å molecular sieves down to 50% when 6.0–8.0 Å zeolites are being used. Moreover, the reactions can be carried out with NaBH$_4$ or NaAlH$_4$, also, without loss of enantiomeric excess and a reduction in the chemical yields.

TABLE I

OPTICALLY ACTIVE 2-ARYL-PROPIONIC ACIDS OBTAINED FROM CHIRAL OXAZOLINES IN THE PRESENCE OF MOLECULAR SIEVES 4.0 Å

| R' | ArX | E E without | with MS 4.0 Å |
|---|---|---|---|
| Me | 4-Br-C$_6$H$_4$-C(CH$_3$)$_2$- | 55,8% | 92% |
| Me | 4-I-C$_6$H$_4$-C(CH$_3$)$_2$- | 61,5% | 90% |
| Me | [4-(CH$_3$)$_2$C-C$_6$H$_4$-]$_2$SO$_4$ | 50% | 85% |
| Me | 6-MeO-2-Br-naphthyl | 45% | 81% |
| Me | 6-MeO-2-Ts-naphthyl | 35% | 79% |
| Me | 4-F-C$_6$H$_4$-C$_6$H$_4$-4-Br | 41% | 81% |
| Me | 6-HO-2-Br-naphthyl | 42% | 90% |
| Me | 3-Br-6-MeO-2-Br-naphthyl | 39% | 85% |

EE = Enantiomeric Excess; solvent: CH$_2$Cl$_2$, temperature 0° C.

A detailed mechanistic rationals for the induction of asymmetry by chiral oxazolines have been published by M. A. Hoobler, D. E. Bergbreiter and M. Newcomb, *J. Amer. Chem. Soc.* 100, 8182, 1978.

Table II lists the enantiomeric excess and chemical yields of S-aryl-propionic acids for several compounds prepared according to this invention. The optical purity can be improved by recrystallizing the substances from ethyl acetate, or for compounds prepared having a low melting point, i.e. S-(+)-2-[4-isobutylphenyl] propionic acid, by distillation at high vacuum (~0.05 mm Hg). The impurities are not due to the enantiomeric form R, they are caused from contamination from reaction products. After re-crystallization of the products in Table II, the S-enantiomers have an optical purity of 98–99% as measured by NMR-methods and by optical rotation.

TABLE II
OPTICALLY ACTIVE 2-ARYL-PROPIONIC ACIDS OBTAINED FROM CHIRAL OXAZOLINES

| R' | R$^{10}$ | ArX | yield (%) | E E | Solvent |
|---|---|---|---|---|---|
| Me | Me | 4-tBu-C$_6$H$_4$-Br | 80 | 98% S | CH$_2$Cl$_2$ |
| Me | n-Butyl | 4-iPr-C$_6$H$_4$-I | 75 | 99% S | THF |
| Me | n-Octyl | (iPr-C$_6$H$_5$)$_2$SO$_4$ | 85 | 86% S | 1,4-Dioxane |
| Me | Me | 4-tBu-C$_6$H$_4$-Ts | 68 | 90% S | CH$_2$Cl$_2$ |
| Me | Me | 6-MeO-2-Br-naphthyl | 70 | 98% S | CH$_2$Cl$_2$ |
| Me | Me | 6-MeO-2-Ts-naphthyl | 70 | 92% S | n-Hexane |
| Me | Me | 3-phenoxy-phenyl-Br | 75 | 85% S | CH$_2$Cl$_2$ |
| Me | Me | 4-Cl-C$_6$H$_4$-Br | 80 | 90% S | n-Hexane / n-Heptane |
| Me | Me | 3-Cl-6-MeO-2-Br-naphthyl | 75 | 85% S | CH$_2$Cl$_2$ / Petrolether |
| Me | Me | 6-HO-2-Br-naphthyl | 80 | 80% S | n-Hexane / CH$_2$Cl$_2$ |
| Me | Me | 4'-F-biphenyl-4-Br | 75 | 95% S | n-Hexane / CH$_2$Cl$_2$ |

In addition it is preferred that R''' is a bulky group, e.g. isobutyl- or n-octyl group. In such a case, the reaction is facilitated to form an enantiomeric excess and the reaction with lithium containing base can be performed at temperatures between 0°–20° C. Thus, for example the reaction with R'''=n-octyl, and Ar=4-isobutylphenyl or Ar=6-methoxy-2-naphthyl with LDA in THF can be performed at 0° C. or 20° C., respectively in the presence of molecular sieves having a ratio of MS 4.0 Å to oxazoline of >1 g/mol and no reduction in ee has been observed; moreover, in both cases the reaction has been completed in 5 minutes. Furthermore, the addition of Ar-Hal with Ar=4-isobutylphenyl or 6-methoxy-2-naphthyl in CH$_2$Cl$_2$ can be performed at 0° or 20° C., respectively, instead of −20° C. to −30° C. according to Scheme I. There is no loss in chemical yields (almost 85%–90%) and optical purity of the corresponding 2-(S)-aryl-propionic acids.

The presence of molecular sieves also appear to facilitate the present process and improves the yield of the aryl propionic acid. When absent, the catalytic reaction provides products of only 50% ee in general according to Table I, as compared with over 90% ee in their presence. Accordingly, the molecular sieves not only facilitate ligand exchange to form the S-formation of the oxazoline transition with the lithium containing base, e.g., LDA, but also the appropriate substitution with Ar-Hal yielding the S-aryl-propionic acids.

Another method for preparing S-2-aryl propionic acids with the support of 2-oxazolines makes use of the complex of LiALH$_4$ or NaAlH$_4$ and 2-alkyl-(4S,5S)-alkoxy-5-phenyl-2-oxazolines according to the formula:

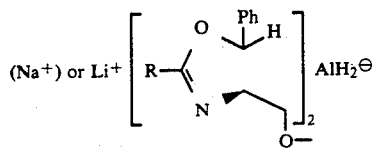

as a chiral reducing reagent for the reduction of the unsymmetric ketone of the general formula:

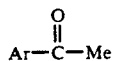

wherein Ar and Ph are as defined hereinabove. As indicated hereinabove, Ar is a monocyclic, polycyclic or orthocondensed polycyclic aromatic group having up to 14 ring carbon atoms and up to a total of 18 carbon atoms. The Ar groups may be monocyclic, bicyclic or polycyclic and may be unsubstituted or substituted with such groups as lower alkyl, aryl, lower arylalkyl, hydroxy, lower alkoxy or halo. It is preferred that the Ar groups contain 6–10 ring carbon atoms. Examples of unsubstituted Ar groups are phenyl, α-naphthyl, β-naphthyl and anthryl. Especially preferred Ar groups 4-isobutylphenyl
6-methoxy-2-naphthyl
3-phenoxy-phenyl
2'-fluoro-4-diphenyl
4'-fluoro-4-diphenyl
5-chloro-6-methoxy-2-naphthyl
5-bromo-6-methoxy-2-naphthyl
4-chloro-phenyl
2',4'-difluoro-4-diphenyl
6-hydroxy-2-naphthyl
5-bromo-6-hydroxy-2-naphthyl
5-fluoro-6-hydroxy-2-naphthyl
5-fluoro-6-methoxy-2-naphthyl
2,2'-difluoro-4-diphenyl Ph is a phenyl group or phenyl substituted with a lower alkyl group. Examples include phenyl, tolyl, xylyl, phenethyl and the like. The preferred Ph group is phenyl.

R as defined herein is a lower alkyl group containing 1–6 carbon atoms or Ph. The preferred R groups are ethyl, n-propyl, n-butyl and phenyl.

An examplary procedure is shown in Scheme II.

The reduction of the unsymmetrical ketone is carried out in a solvent that is polar or weakly polar. The preferred solvent is THF. The reaction is carried out at a temperature effective for the reduction to take place, preferably at a temperature ranging from −75° to 0° C., with a more preferred temperature ranging from −20° to −60° C. The reaction is preferably run under anhydrous conditions and in an inert atmosphere, such as under nitrogen or argon. In addition, the reaction is preferably run in the presence of a dry agent, such as molecular sieves. The molecular sieves of 3.0 Å to 8 Å can be used, but molecular sieves of 4–5Å, especially 4 Å is especially preferred. The molecular sieves should be used in effective amounts, a molecular sieve in a ratio of approximately 0.5 to 10 g molecular sieves to 100 umol to 200 umol of oxazoline complex. It is preferred that the ratio is 0.5 to 10 g of 4 Å molecular sieves to 40 umol to 300 umol of oxazoline complex. Finally, it is especially preferred that the ratio is approximately 1–3 g of 4.0 Å molecular sieves to 100–200 umol of chiral reducing agent. Finally, it is most preferred that the ratio is approximately 1.5 g molecular sieves of 4.0 Å to 150 umol of chiral reducing agent.

From the 2-aryl methyl-2-hydroxy ethane that is formed from the above step, the 2-aryl propionic acid can be formed therefrom in a variety of ways. Scheme II exemplifies one such route.

Stereospecific halogenation of the enantiomeric carbinol, R or S, by keeping retention of configuration of the chiral carbon can be performed either with thionyl-chloride or thionylbromide, or cyanuric chloride in high chemical yields (almost quantitative) and high optical purity. Preferably, the halogenation is performed in 1,4-dioxane, water-free, when using high amounts of the carbinols, whereas dry pyridine can be used also. The enantiomeric carbinols are normally dissolved in 1,4-dioxane at 20° C. by adding the stoichiometric amounts of thionyl-chloride dropwise under continuous mixing over a period of time of one hour. The reaction should continue in the case of thionylchloride or bromide for 30 minutes further. The excess of SOCl$_2$ or SOBr$_2$ is eliminated by passing a dry stream of nitrogen through the reaction solution at 20° C. for approximately five hours, unless the R- or S-enantiomeric chloride is being recovered through high vacuum distillation.

A typical procedure for preparation of the enantiomeric chloride involves heating of the enantiomeric carbinols with powdered cyanuric chloride (1 mol) to 10°–20° C. above the boiling point of the carbinols or in the presence of a base (0.5 mol NaOCH$_3$ or NaOBu). After the addition (ca. 1–1.5 h), the reaction mixture is cooled, filtered and distilled under high vacuum. The results according to this procedure indicate that no isomerization or racemization has occurred.

SCHEME II
STEREOSPECIFIC SYNTHESIS OF S-2-ARYL-PROPIONIC ACIDS THROUGH REDUCTION OF THE APPROPRIATE KETONE BY OXAZOLINE

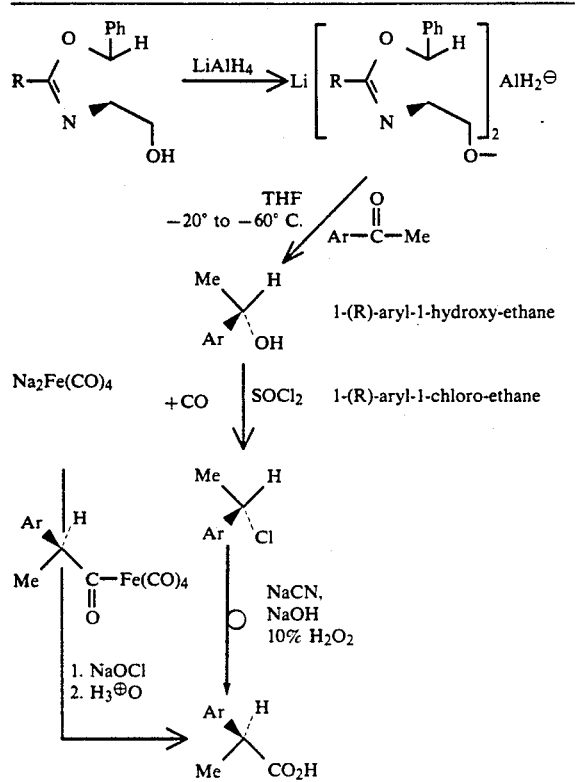

"R" in the Li-oxaloine complex is alkyl, aralkyl, e.g., n-butyl, n-propyl, ethyl, phenyl and the like.

Ar is as defined hereinabove. It is preferred that Ar is 6-methoxy-2-naphthyl, isobutyl-phenyl, phenoxyphenyl, 6-hydroxy-2-naphthyl, 5-bromo-6-hydroxy-2-naphthyl.

Another way of using optically high pure enantiomers, R or S, from 1-aryl-haloethane being produced easily according to this invention, of 2-aryl-alkanoic acids, especially 2-aryl-propionic acids, is the direct conversion of the 1-aryl-halides with sodium tetracarbonyl-ferrate(-II) ($Na_2Fe(CO)_4$) in the presence of triphenyl-phosphine ($Ph_3P$) and subsequent oxidation with iodine-$H_2O$ to the corresponding acid, or in the presence of a secondary amine to yield the optically pure amide. An exemplification of this preparation is outlined in Scheme III. In Scheme III, Ar is depicted as

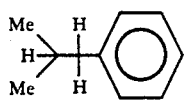

but any of the Ar groups defined herein can be used. The reagent $Na_2Fe(CO)_4$ can be prepared by treatment of $Fe(CO)_5$ with sodium amalgam (NaHg) in THF.

Another method for the conversion of the enantiomeric pure 1-aryl-haloethane to the acid derivatives also makes use of $Na_2Fe(CO)_4$ also, in the presence of CO. The 1-aryl-1-hydroxy ethane is reacted with $Na_2$-$Fe(CO_4)$ in the presence of CO followed by treatment of the product prepared therefrom with oxygen or sodium hypochlorite and subsequent hydrolysis. This series of reactions of the intermediate (IV) with oxygen or sodium hypochlorite and subsequent hydrolysis produces the corresponding enantiomeric acid with high optical purity and chemical yields of 75–80%. An exemplification of this reaction scheme is depicted in Scheme II.

The application of the complex between sodium-tetra-cyano-ferrate (II) and phosphine ($Ph_3P$) or carbon monoxide, respectively, is useful especially in the synthesis of 2-alkyl-alkanoic acids, because of its high nucleophilicity and the ease of the integrating inversion reaction of this system. So the halides obtained according to this invention, and the tosylates react with $Na_2$-$Fe(CO)_4$ with typical $SN_2$ kinetics, stereochemistry (inversion) in order to produce coordinated saturated anionic $d^8$ alkyl iron (0) complexes. This procedure provides routes from alkyl and acid halides to alkanes, aldehydes, ketones and stereo-specific carboxylic acids, including their derivatives.

SCHEME III

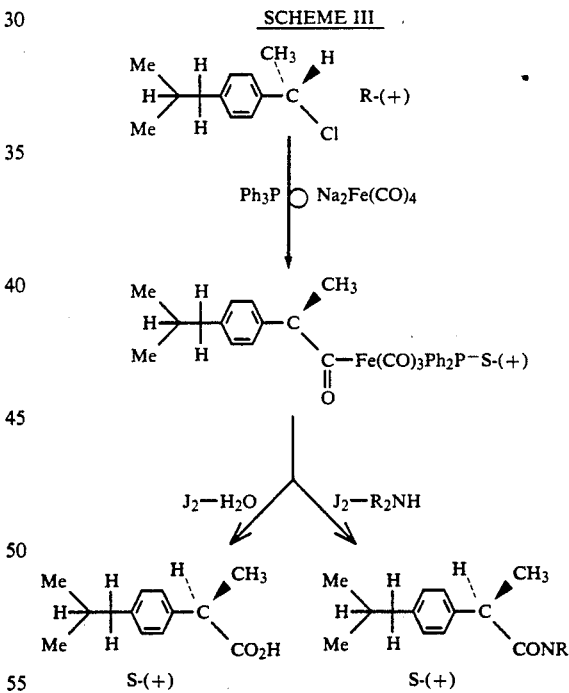

Once having established a stereoselective method of reducing the ketone to the corresponding enantiomeric alcohol with high optical purity (>97%) and very high chemical yields (>90%), it is possible to produce either directly from the R-alcohol the S-carboxylic acids or via the R-form of the halide (Scheme IV, V) the corresponding nitrile in the presence of NaCN and DMSO at effective temperatures. It is preferred that the temperature ranges from 40° C. to 50° C.

SCHEME IV

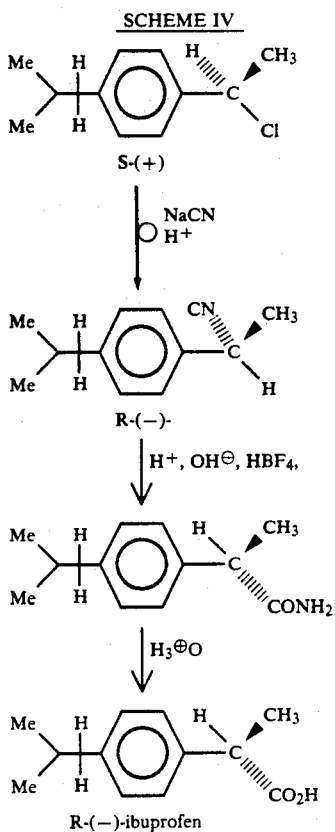

SCHEME V

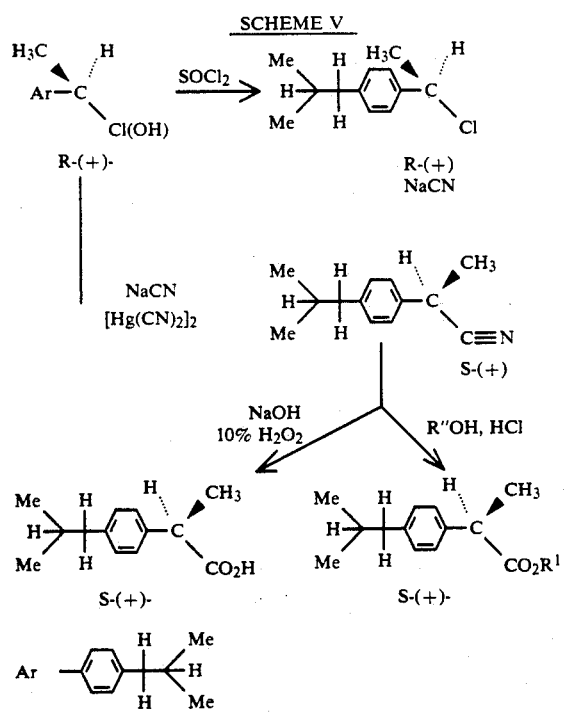

Subsequently the enantiomeric S-nitriles can be hydrolyzed to give either amides or the corresponding acids. When the S-acid is desired, the reagent of choice is aqueous NaOH containing about 6–8% $H_2O_2$, though acid-catalyzed hydrolysis can also be carried out successfully. The chemical yields can be improved by using a strong polar aprotic complexing solvent such as HMPT for the synthesis of 2-aryl- propionic acids, or by complexing the cyanide ion as a quaternary ammonium salt. This process has the advantage that the condensation can easily be monitored in a continuous process e.g. as $Et_4N^+CN$, or $C_6H_5\cdot CH_2(Me)_3N^+CN$, applying phase transfer catalysis, or by using crystals such as dicyclo-hexano-18-crown-6.

The production of the S-enantiomeric nitriles by $Et_4N^+CN$ or Na(K)CN can be performed according to known methods as described by, e.g. J. M. Teulon et al., J. Med. Chem. 21 (9) 901, (1978), N. Tokutake, Chem. Abstracts 88, 50512f; S. Kothicki et al., Chem. Abstracts 90, 1036526; H. Kobler et al., Liebig's Ann. Chem. 1946, (1978); T. Amano et al., Chem. Abstracts, 13, 2611 p; Nissan Chemical Industries, Ltd, Chem. Abstracts, 101 90603e, (1984), Nissan Chemical Industries, Ltd., Chem. Abstracts, 101, 6855 h; J. A. Foulkes and J. Hutton, Synth. Commun. 9 (7), 625 (1979). However, these procedures mentioned lead to racemates, only.

Usually, the 2-aryl-alkanoic acids especially those of the 2-aryl-propionic acids, are scarcely soluble in water; therefore at the end of the reactions the optically active 2-aryl-propionic acids can easily be isolated by filtration, etc. However, avoiding filtration, crystallizations from organic solvents etc., a suitable method for further purification is distillation at high vacuum (~0.06 mm Hg) for 2-aryl-propionic acids, i.e. S-(+)-ibuprofen, having a low melting point. Furthermore, a pharmaceutical product as pure as required by U.S. Pharmacopeia is obtained by acid-base treatment of the product isolated by filtration, evaporation or distillation in high vacuum.

Moreover, another procedure which brings about the asymmetric reduction of unsymmetrical ketones of the formula:

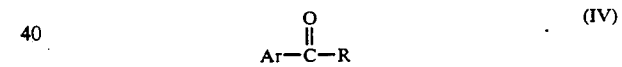

employs a complex between boronhydride ($BH_3$) and tetrahydro-furan (THF) in the presence of 2-alkyl-4-alkoxy-S-phenyl-2-oxazoline according to Scheme VI at effective working temperatures. It is preferred that the temperature ranges from 10°–20° C. The yields are 99.7% with an enantiomeric excess of 97%.

SCHEME VI

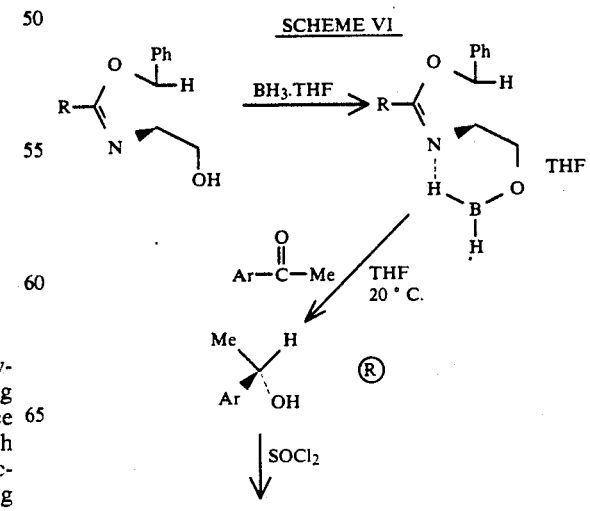

-continued
SCHEME VI

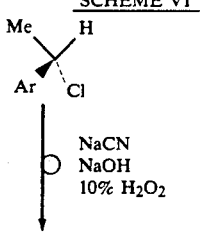

SCHEME VII

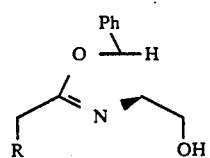 + 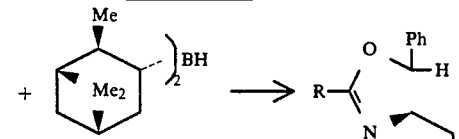

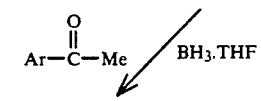 BH₃·THF

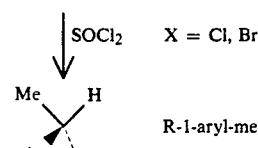  R-1-aryl-1-hydroxy-ethane

↓ SOCl₂    X = Cl, Br

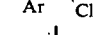 R-1-aryl-methyl-1-chloro-ethane

↓ NaCN, NaOH 10% H₂O₂

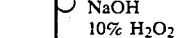 S-2-aryl-propionic acid

the retention of chiral conformation, reaction of sodium cyanide yielding the corresponding nitrile by changing the chiral configuration and subsequent hydrolysis to the corresponding carboxylic acid of desired R- or S- configuration. A representative example is depicted in Scheme VII.

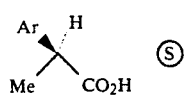

Furthermore it has been found that diisopinocamphenylborane, which can easily be prepared from borane-methyl sulfide complex in THF and α-pinene, is also a suitable chiral complex with oxazolines for the reduction of unsymmetrical ketones having a prochiral carbon atom (Scheme VII) using BH₃·THF as a reducing agent. Either the (+) or (−) pinene can be used to yield the corresponding optically active IPC₂BH derivatives for producing the corresponding R- or S-enantiomers of 2-aryl-methyl-2 hydroxyethane according to Scheme VII. Again, Ar is as defined hereinabove. Molecular sieves are not necessary for the reduction of the unsymmetrical ketone by applying BH₃THF since no improvement of ee has been observed in chemical yields. Again, once the 1-aryl-1-hydroxyethane is formed, the aryl propionic acid can be prepared by the routes outlined hereinabove. Alternatively, the subsequent chemical steps from the 1-aryl hydroxy ethane in the chemical synthesis include halogenation by keeping The invention will be described in greater detail in conjunction with the following specific examples.

EXAMPLE 1

Preparation of trans-(4S,5S)-2-ethyl-4-hydroxymethyl-5-phenyl-2-oxazoline (I)

To a mixture of 130 g (0.785 mol) of (1S,2S)-(+) 2-amino-1-phenylpropane-1,3-diol and 180 g (0.102 mol) of triethyl or thiopropanoate in 750 ml of 1,2 dichloroethane are being added under continuous stirring, and subsequently heated under reflux for 5 hours. Cooling to room temperature and leaving for 5 minutes at 0° C. a crystalline product is obtained of 175 g. The product is purified by recrystallization from a solution of THF or THF/Ether (70/30 v/v). The recrystallized material can be treated with charcoal, filtered and concentrated, and cooled at −20° C., where a crystalline material precipitates. The yield of the product is 170 g, having a melting point of 68.7° C., $[\alpha]^{22}$ −135.5° (C 10.0 in CHCl₃).

EXAMPLE 2

Preparation of (4S,5S)-2-ethyl-4-methoxymethyl-5-phenyl-2-oxazoline (II)

180 g of I are dissolved in 2 L of dry THF at 20° C. To this solution a suspension of sodium hydride (110 mol) in benzene is being added dropwise under continuous stirring in the presence of 4.0 Å molecular sieves under nitrogen at room temperature. The evolution of hydrogen is controlled by volumetric measure. After the complete edition of NaH in benzene, the mixture is heated at 50° C. for one hour and cooled to 20° C. To this solution a solution of methylbromide or methyliodide (170 g, 1,3 mol) in 150 ml THF is added dropwise through a funnel under continuous stirring over a period of time of two hours. This solution is slowly poured into 3 L of ice-water, and then extracted with ether. The combined ether extracts are dried over anhydrous $Na_2SO_4$ and molecular sieves (4.0 Å), concentrated to an oil which is distilled in vacuo to yield a product of 90% yield, having a boiling point of 91° C./0.20 mm Hg.

EXAMPLE 3

Preparation of S-(+)-2-[4-isobutylphenyl] Propionic Acid

A solution of the compound II (155 g, 0.71 mol) in THF (1.6 L) under nitrogen is cooled to −75° C. in a dry-ice-acetone bath. A solution of 0.8 mol of lithium diisopropylamide, derived from 98 ml of diisopropylamine and 300 ml of 2,3M butyllithium (methyllithium) in 750 ml of dry THF is prepared, and added under continuous stirring in the presence of 4.0 Å molecular sieves to the solution of II in dry THF. Stirring is continued for half an hour at −75° C. and 4isobutylphenyliode (bromide) of the amount of 237.6 g (1.95 mol) in 300 ml THF (dry) is added over a period of time of 10 minutes. The resulting, colorless solution is stirred at this temperature for one hour, then subsequently permitted to reach 20° C. The reaction mixture is poured into 3L of saturated aqueous sodium chloride solution, extracted with several portions of petrolether or ether, dried over $Na_2SO_4$ or molecular sieves, (4.0 Å) and distilled in vacuo at 0.1 mm Hg to yield 90% of 2-(1-methyl-4-isobutylphenyl)-4-methoxymethyl-5-phenyl-2-oxazoline, having $[\alpha]^{24}$ −40.5° (c 10.1 in $CHCl_3$) IR (film) 1671 $cm^{-1}$, NMR ($CDCl_3$, TMS) δ7.33 (s, 5H), 5.33 (d, J=7HZ, 1H), 4.33-3.93 (9, 1H), 3.80-3.33 (m, 2H) 3.43 ( 3H), 2.87-2.33 (m, 1H), and 2.00-0.68 (m, 12H).

The oxazoline (170 g) is dissolved in 2.0 L of 1.5M sulphuric acid, and heated to reflux for 3 hours, or until the solution becomes homogeneous. After heating the solution is cooled to 20° C. and either extracted with $Et_2O$ or petrolether, or diluted by water under the addition of $NaHCO_3$ keeping the solution at 0° C. because of avoiding the formation of an oil. The formed precipitate is washed with cold water until neutralized as well as the watery filtrate shows a pH 1.0. The collected precipitate is transferred to high vacuum distillation. The liquid of S-(+)-ibuprofen is distilled at 2 mm Hg (0.06-2 mm Hg) at 120°-90° C., to yield 91.2 g (90%) of S-(+)-ibuprofen. NMR ($CDCl_3$), s 0.91, (d,J=7H, 6H) 1.50 (d,J=8Hz, 3H), 1.84 (nonet, 1H), 2.96; (brd, 27H7, 2H), 3.72 (g, 1H), 7.01-7.32 (AA′BB′, 4H), 9.78 (br. s 1H). $[\alpha]^{25}$ +58° (95%, EtOH); m.p. 51°-52° C.; (1S,2S)-(+)-2-amino-1-phenylpropane-1,3-diol can be recrystallized from methanol (1.5 parts) by adding three parts of ethyl acetate and cooling to 0° C. The pure material has a m.p. 112° C., $[\alpha]^{22}$ 26.6° (C 10.0 in MeoH).

EXAMPLE 4

Preparation of (4S, 5S)-2-Ethyl-4-Butoxymethyl-5-phenyl-2-Oxazoline 100 g of trans-(4S, 5 S)-2-ethyl-4-hydroxymethyl-5-phenyl-2-oxazoline are dissolved in 750 ml of dry THF ($CH_2Cl_2$) at 20° C.(15° C.) Molecular sieves (4.0 Å) in the amount of 5 g are added under dry nitrogen and thorough stirring. Through a dopping funnel and continuous stirring of the solution a suspension of sodium hydride (61.5 mol) in benzene ($CH_2Cl_2$) or cyclohexane are being added in a dropwise fashion. The evolution of hydrogen can be controlled by volumetric measurements in order to monitor the completion of addition of NaH. The mixture (under stirring) is heated at 50° C. for less than one hour (20-30 minutes), subsequently cooled to 20° C., and finally a solution of n-butylbromide (160 g, 1,3 mol) in 100 ml THF is being added dropwise through a dropping funnel over a period of time of one hour. This solution is slowly poured into one liter of ice/water, extracted with ether or petrolether, and the combined extracts are dried over anhydrous $Na_2SO_4$, concentrated to an colourless oil, which can be distilled in vacuo to yield a product of 80 % yield, m.p 115°-120° C. (0.3 mm) Hg.

EXAMPLE 5

Preparation of S-(+)-2-[4-isobutylphenyl]Propionic Acid

A solution of the compound (4S, 5S)-2-Ethyl-4-butoxymethyl-5-phenyl-2-oxazoline (example 4) is dissolved in 1.0 L dry THF (100 g, 0.45 mol) under nitrogen, and cooled to −20° C. in a ice acetone bath. A solution of 0.55 mol of lithium diisopropylamide in 500 ml of dry THF is being added under continuous stirring in the presence of 5 g molecular sieves (4.0 Å) dropwise through a dropping funnel. The stirring is continued for 30 minutes at −20° C., and 4-isobutylphenylbromide of 153.3 g (1.26mol) in 150 ml dry THF is added over a period of time of 10 minutes. The resulting colourness solution is stirred at −20° C. for 20 minutes, then subsequently the temperature is raised to approximately 20° C. within 20 minutes The reaction mixture is poured into 2 L of saturated aqueous NaCl solution, extracted with petrolether, dried over $Na_2So_4$, and subsequently distilled at 0.5 mm Hg to yield 90% of the oxazoline, having $[\alpha]_{589}^{24}$ −38.5° C. (5.5 in $CHCl_3$).

The oxazoline (100 g) is dissolved in 1.0 L of 1.5M sulphuric acid, heated under reflux fo 2 hours, or until the solution becomes homogeneous. After heating the solution is cooled to room temperature, a fluffy precipitate developed which can be extracted with $Et_2O$ or petrolether, or further diluted with cold water (0° C.) under the addition of $NaHCO_3$ by keeping the entire solution at 0° C. because of avoiding the formation of an oil of the resulting product of S-(+)-ibuprofen, or by keeping the pH at 1.0. The collected precipitate can be recrystallized from various solvents, e.g. $Et_2O$, petrolether, EtOH, aceton etc. yielding in the average 90 g (90%) of S-(+)-ibuprofen.

(1S, 2S)-(+)-2-amino-1-phenylpropane-1,3-dione can be recovered from the supernatant as described in example 3.

EXAMPLE 6

Preparation of S-(+)-(6-Methoxy-2-Naphthyl)-Propionic Acid

A solution of trans-(4S, 5S)-2-ethyl-4-methoxy-methyl-5-phenyl-2-oxazoline (100 g, 0.45 mol) in 750 ml of dry THF under nitrogen is prepared, and cooled to −10° C. in an ice-acetone bath. A solution of 0.60 mol of lithium diisoproylamide in 250 ml of dry THF is being added under continuous stirring in the presence of 3 g molecular sieves (4.0 Å) dropwise through a dropping funnel. The stirring is continued for 30 minutes at −10° C., and 6-methoxy-2-bromo-naphthalene (315 g, 1.25 mol) dissolved in 300 ml dry THF, is being added dropwise over a period of time of 10 minutes. The resulting solution is kept for 30 minutes at −10° C. after addition of the naphthyl-halide, subsequently raising the temperature to +20° C. within 20 minutes. The reaction mixture is poured into 1 L of saturated aqueous NaCl solution, extracted with petrolether, dried over $Na_2SO_4$ (all operations at 20°-25° C.), and the combined extracts cooled to 0° C., yielding a fine crystalline preparation of the oxazoline, having $[\alpha]_{589}^{24}$ −41.5° C. (4.0 in $CHCl_3$). Yield 85%, m.p. 51° C. (corrected). The naphthyl-oxazoline (100 g) is dissolved in 500 ml of 1.5M sulphuric acid, heated under reflux for 1 hour until the solution becomes homogeneous. After the heating step the solution is cooled to room temperature, where normally a fine crystalline precipitate developed which can be filtered off easily, being worked with cold water (0°-5° C.), then with $NaHCO_3$ saturated solution (0°-5° C.) and finally with cold water. The chemical yield is 85%, the optical purity 97%.

Recrystallization of the raw material with mp 152°153° C. yields a crystalline specimen of S-(+)-naproxen of 154° C. (lit mp 152°-154° C. $[\alpha]_D^{25}$ +65 0° C. (1,08 $CHCl_3$), NMR ($CHCl_3$); 1,6(D, 3H, CH-$CH_3$); 3,92 (S, 3H, $OCH_3$), 3,88 (g,TH,CH) and 7-7.9 (m, 6H, aromatic). (1S, 2S)-(+)-2-amino-1-phenylpropane-1,3-diol can be recovered from the supernatant as described in example 3.

EXAMPLE 7

Preparation of S-(+)-2-(5-Bromo-6-methoxy)-2-Naphthyl-Propionic Acid

A solution of trans-(4S, 5S)-2-ethyl-4-methoxymethyl-5-phenyl-2-oxozoline (50 g, 0.25 mol) in 350 ml of dry THF (or 1,4 dioxane) under dry nitrogen is prepared and cooled to −20° C. in an dry ice/acetone both A solution of 0.55 mol of lithium diisoproplyamide in 100 ml dry THF is being added under continuous stirring in presence of 3.0 g molecular sieves (4.0 Å) dropwise through a dropping funnel. The stirring is continuous for half an hour at 0° C., and 5-bromo-6-methoxy-2-cloro-naphthalene (168 g, 0.67 mol), which has been dissolved in 200 ml of dry THF, is added dropwise through a dropping funnel over a period of 10 minutes. The resulting solution is kept for 30 minutes at 0° C. after the addition of the naphthylhalide, subsequently raising the temperature to +20° C. within 30 minutes. The reaction mixture is poured into 1 L of saturated aqueous NaCl solution, extracted with petrolether, dried over $Na_2SO_4$ (all operations at 20°-25° C.), and the combined extracts cooled to 0°-5° C., yielding a fluffy precipitate of the oxazoline, having an $[\alpha]_{589}^{24}$ −35.9° C. (3.0 in $CHCl_3$), yield 81%, mp 71° C. The naphthyl-oxazoline (50 g) is dissolved in 250 ml of aqueous 1.5M sulphuric acid, heated under reflux for 60 minutes until the solution becomes homogeneous. After the heating step the solution is cooled to room temperature, where a fine crystalline precipitate developed, which can be filtered off, being washed with cold water (0°-5° C.), followed by a wash with saturated $NaHCO_3$ solution, and finally with cold water. The chemical yield is 80%, the optical purity 97-98%; m.p. 167.5° C., and $[\alpha]_D^{24}$ −42.5° [c 0,6% $CHCl_3$).

EXAMPLE 8

Preparation of S-(+)-Phenyl Propionic Acid

A solution of 100 g (4S, 5S)-2-ethyl-4-butoxymethyl-5-phenyl-2-oxazoline (see example 4) in 1,5 L of dry THF is prepared and cooled to −30° C. in the presence of pure nitrogen in a dry ice-acetone both. A solution of 0.75 mol of lithium diisopropylamide, prepared by reacting 95 ml of diisopylamine and 205 ml of 2.4M butyllithium or methyllithium in 600 ml of dry THF, is added dropwise under continuous stirring in the presence of 2,5 g 4,0 Å molecular sieves to the oxazoline solution. Stirring is continued for approximately 30 minutes at −50° C., and phenylbromide or phenyliodine of 340 g (1,80 mol) in 200 ml THF (dry) is being added over a period of time of 10 minutes. The resulting, colorless solution is brought to 20° C. within 45 minutes under stirring, the mixture is poured into 1 L of saturated NaCl solution, extracted with several positions of petrolether, dried over $Na_2SO_4$, and subsequently distilled under reduced pressure to yield 20% of the oxazoline, having $[\alpha]_{589}^{24}$ −29.5 (1,0 in $CHCl_3$).

The so prepared oxazoline (50 g) is dissolved in 1.0 L of 1.0M sulphuric acid, heated under reflux for 1.5 hours until the solution becomes homogeneous. The transparent solution is cooled after the heat step to room temperature where normally a fluffy precipitate developed. The collected precipitate can be dissolved in $Et_2O$ or acetone, or further washed with cold water (0° C.) by keeping the entire solution at 0° C. Recrystallization can be performed from methanolic solutions, yielding S-(+)-phenyl propionic acid (85% chemical yield), having an $[\alpha]_{589}^{24}$ +74° (c=1.7 in $CHCl_3$), an optical purity of 98,5% as determined by NMR techniques.

EXAMPLE 9

Preparation of S-(+)-2-(2-fluoro-4-biphenyl) Propionic Acid

A solution of trans-(4S, 5S)-2-ethyl-methoxy-methyl-5-phenyl-2-oxazoline (50 g, 0.25 mol) in 200 ml of dry THF under dry $N_2$ is prepared and cooled to −20° C. in a dry ice/acetone bath. A solution of 0.55 mol of lithium diisopropylamide in 100 ml dry THF is being added under continuous stirring in the presence of 3 g molecular sieves (4,0 Å) dropwise through a dropping funnel. The stirring is continued for 30 minutes at 0° C., and subsequently 2-fluoro-1-chloro-4-biphenyl which has been dissolved in 100 ml of dry THF (372 g, 1.8 mol), is added dropwise through a dropping funnel over a period of 10 minutes. The resulting solution is kept for 30 minutes at 0° C. after the addition of the biphenyl-halide the temperature is being raised to 20° C. within 30 minutes. The reaction mixture is poured into 1 L of saturated aqueous NaCl solution, extracted with petrolether, dried over $Na_2SO_4$ (all operations at 20°-25° C.), and the continued extracts cooled to 0°-5° C., yielding a precipitate of the oxazoline, having an $[\alpha]_{589}^{24}$ −3.15°60 C. (C 1.5 in CHCl$_3$), yield 85%, m.p. 87° C.

The biphenyl-oxazoline (20 g) is dissolved in 150 ml of aqueous 1.5M sulphuric acid, heated under reflux for 60 minutes until the solution becomes homogeneous. After the heating step the solution is cooled to 20° C., where a fine crystalline precipitate developed, which is being filtered off, washed with cold water (0°-5° C.) several time, and recrystallised from ethylacetate. The chemical yield was 75%, the optical purity 98%, m.p. 112,5° C., and $[\alpha]_D^{24}$ −47.5° (c 2,5 in CHCl$_3$).

EXAMPLE 10

Preparation of S-(+)-2-(5H-[1]benzopyrano[2,3 b]pyridin-7-Y)Propionic Acid

A solution of (4S, 5S)-2-ethyl-4-butoxymethyl-5-phenyl-2-oxazoline is dissolved in 500 ml of dry THF (100 g, 0.45 mol) under nitrogen, and cooled to −20° C. in an ice-acetane bath. A solution of 0.55 mol of lithium diisopropylamide in 500 ml of dry THF is being added under continuous stirring in the presence of 5 g molecular sieves (4,0 A), dropwise through a suitable funnel. The stirring is continued for 30 minutes at −10° C., and 5H-[1]-benzopyrano[2,3-b]-7-bromo-pyridine of of 1,05 mol in 100 ml dry THF is added over a period of time of 15 minutes. The resulting yellow solution is stirred at −20° C. for continuing 20 minutes, then subsequently the temperature is raised to approximately 20° C. within 20 minutes. The reaction mixture is poured into 1 L of saturated brine solution, extracted with 1,4 dioxone, dried over Na$_2$SO$_4$, and subsequently distilled under reduced pressure to yield 82% of the oxazoline, having $[\alpha]_{589}^{24}$ −31.5 (1,5 in CHCl$_3$)

The oxazoline (50 g) is dissolved in 1,0 L of 1.0M sulphuric acid, heated under reflux for 1½ hours until the solution becomes homogeneous. The solution is cooled after the heat step to room temperature where normally a fluffy precipitate developed, which can be extracted with Et$_2$O or 1,4-dioxane, or further washed with cold water (0° C.) under the addition of 15 g NaHCO$_3$ (per 1 L) by keeping the entire solution at 0° C. because of avoiding the formation of an oily microemulsion. The collected precipitate can be re-crystallized from 1,4-dioxane, yielding in the average 85 g (82%) of S-(+)-pranoprofen, m.p. 184° C., $[\alpha]_{589}^{24}$ +44,1 (C=1,0 methanol). The optical purity was determined to be 98% as observed by NMR techniques.

EXAMPLE 11

Preparation of S-(+)-2-[2-fluoro-4-biphenyl]propionic acid

A solution of (4S, 5S)-S-(+)-2-ethyl-4-butoxymethyl-5-phenyl-2-oxazoline or (100 g) or (4S, 5S)-2-ethyl-4-methoxy-5-phenyl-2-oxazoline (100 g) are dissolved in 700 ml of dry THF under nitrogen, and cooled to −20° C. in an ice/acetone bath. A solution of 0.55 mol of lithium diisopropylamide in 250 ml of dry THF is being added under continuous stirring in the presence of 5 g 4.0 Å molecular sieves dropwise through a dropping funnel. The stirring is continued for half an hour at −20° C., and 2-bromo-2-fluoro-4-biphenyl (206 g, 1,0 mol) dissolved in 100 ml dry THF is added over a period of time of 20 minutes. The resulting solution is continued for stirring at −20° C. for completeness of the reaction for approximately 20 minutes, and subsequently the temperature is being raised to room temperature within 20 minutes. The reaction mixture is poured into 1 L of saturated aqueous NaCl solution extracted with petrolether, dried over Na$_2$SO$_4$, and subsequently distilled under reduced pressure to yield 90% of the oxazoline, having an $[\alpha]_{589}^{24}$ −42.5° (5.0 in CHCl$_3$.

The oxazoline (50 g) is dissolved in 1.0 L of 1.0M sulphuric acid, heated under reflux for 2 hours until the solution becomes transparent. Afterwards the solution is cooled to room temperature where a precipitate developed which can be extracted with Et$_2$O, acetone or petrolether. The extracct are continued precipitated with cold water (0° C.), and subsequently filtered off, washed several times with cold water, and the precipitate can be recrystallized from methanol, yielding a product of 97% optical purity with a chemical yield of 78% $[\alpha]_{589}^{25}$ +47.5° (2,5 in CHCl$_3$).

EXAMPLE 12

Preparation of R-(+)-1-(4-Isobutylphenyl) Hydroxyethane 10 g of (4S, 5S)-2-ethyl-4-hydroxymethyl-5-phenyl-2-oxazoline is dissolved in 100 ml dry THF (0.05 mol) at −20° C. Under continuous stirring in the presence of 1 g molecular sieve (4.0 Å) 50 ml of 0.5 l equivalents of LiAlH$_4$ are added dropwise over a period of 10 minutes by keeping the temperature at −20° C. It is important that the solution is well stirred and after 10 minutes the stirred solution is cooled to −60° C. Through a dropping funnel and under nitrogen and −60° C., 10.0 g (5 mmol) of 1-(4-[n-methylpropyl]-phenyl)ethanone, which has been dissolved in 10 ml of dry THF, are added dropwise under continuous mixing by keeping the temperature at −60° over a period of 30 minutes. The suspension yields a clear colourless solution after addition of the ketone which is left for completing the reaction for another 30 minutes under continuous mixing in the presence of molecular sieves (4.0 Å). The mixture is hydrolysed with 5.0 ml of water after raising the temperature to 20° C., diluted with hydrochloric acid which is added in order to save the chiral oxazoline for later reuse.

The clear solution is extracted with Et$_2$O, leaving the oxazoline in the aqueous phase, and the R-(+)-2-(4-isobutylphenyl)-hydroxy-ethane in the organic phase. The etherol extracts are combined, concentrated and distilled in vacuum (0.1 mm Hg, b.p. 80° C.) which yields a clear colourless fairly viscous liquid (11.5 g, 94% yield), containing no unreduced ketone as measured by HPLC-techniques and confirmed by the absence of the carbonyl infrared stretching frequency. The optical purity is determined by conversion to the MTPA derivative and by measuring the NMR-spectrum gives a value of 98% ee. Neutralization of the oxazoline extract yields recovered chiral (4S, 5S)-2-ethyl-4-methoxymethyl-5-phenyl-2-oxazoline with a boiling point of 90.5° C./0,2 mm Hg, yield 80%.

The recovery of the corresponding trans-(4S, 5S)-2-ethyl-4-hydroxy-methyl-5-pheny-2-oxazoline, having a melting point of 68.2° C., $[\alpha]_{590}^{22}$ −135° (c 11.0 in CHCl$_3$) from the methoxy methyl compound was 70%.

EXAMPLE 13

Preparation of S-(+)-2-[4-Isobutylphenyl] Propionic Acid from the corresponding R-(+)-Hydroxy-Ethane 10 g of R-(−)-1-[4-isobutylphenyl]-hydroxyethane (56 mmol) are dissolved in 20 ml 1.4 dioxane at 20° C. in the presence of molecular sieves 4 Å under stirring. 5.0 ml SOCl$_2$ (=60 mmol), dissolved in 5 ml 1.4-dioxane containing 10 ml $H_2O$, is added dropwise under continuous stirring over a period of 10 minutes by keeping the temperature at 20° C. After one hour the reaction is complete and the thionyl chloride is recovered through evaporation by bubbling $N_2$ through the solution. The S-(−)-1-[4-isobutylphenyl]-chloroethane does not need to be separated since the solution is used immediately for metallation wit Mg or Hg $(OOC.CH_3)_2$. To this solution containing 11 g of S-(−)-1-(−)-[-4-isobutylphenyl]-chloroethane 1.40 g Mg (0.055M) in the presence of iodine is added at 0° C., and after a period of 10–30 minutes a vigorous reaction starts, so sometimes cooling may be necessary in order to avoid Wurtz synthesis and biradical production. The solution turns from light yellow to light brown at the end of the reaction when carbon dioxide is passed through the reaction at 0°–5° C., under continuous mixing. The Grignard compound which is derived from S-(+)-1-[4-isobutylphenyl]chloroethane (or bromoethane when $SOBr_2$ is used) is diluted by $Et_2O$ or THF (or benzene, toluene) when passing dry $CO_2$ through the solution under continuous stirring which is essential for obtaining high chemical yield of optically pure S-(+)-ibuprofen. The continuous addition $CO_2$ to the S-Grignard compound and the production of the S-carboxylic acid makes it necessary to add dry 1,4 dioxane continuously as the S-carboxylic acid develops and saturates the solvent. After 20 minutes the reaction is complete, is separated from solid residues and is transferred to high vacuum distillation. The solution is concentrated and distilled at 2 mmHg (0.06–2 mm Hg) at 120°–98° C., to give 9.30 g (80%) of S-(+)-ibuprofen: NMR ($CDCl_3$) S 0.91 (d,J=7H, 6 H), 1.50 (d,J=8Hz, 3 H), 1.84 (nonet, 1H), 2.96 (brd, 27H7, 2H), 3.72 (g, 1H) 7.01–7.32 (AA'BB',4H), 9.78 (br.s1H). $[\alpha]_D^{25}$ +58° (95%, EtOH). or Alternatively through

EXAMPLE 14

S-(+)-ibuprofen is prepared by reacting the 10 g R-(+)-1-[4-isobutylphenyl]-chloroethane (50,5 mmol) in 25 ml EtOH and 5 ml of water with 2.95 g (60 mmol) sodium cyanide by dropwise addition of the cyanide solution.

The mixture is refluxed for one hour and allowed to cool down to 20° C. The precipitated sodium chloride is filtered off and the supernatant, containg water and EtOH are dried and EtOH is distilled from the remaining liquid, which contains the S-(+)-1-[4-isobutyl phenyl]-ethyl cyanide. (Chemical yield 88%). This S-(+)-cyanide is dissolved in 15 ml EtOH and 30 ml water, which contains 9 g (0,45 mol) sodium hydroxide and 10% (w/w) $H_2O_2$ and heated under reflux conditions for one hour. After cooling to room temperature the reaction mixture is diluted with 100 ml water until a clear and transparent solution appears. This solution is cooled down to 0° and 100 ml of diluted hydrochloric acid is subsequently added, when S-(+)-ibuprofen precipitates as small crystals. The S-(+)-ibuprofen crystals are collected, washed with dilute hydrochloride acid and dried over $CaCl_2$. The chemical yield is 94% and the melting point was 51°–54° C. $[\alpha]_D^{20}$ +60° (95% EtOH).

EXAMPLE 15

Preparation of S-(+)-2-(5-bromo-6-Methoxy-2-Naphthyl) Propionic Acid

Performing the reduction of the corresponding ketone with (4S, 5S)-2-ethyl-4-methoxymethyl-5-phenyl-2-oxazoline-$LiAlH_4$ complex, as described in example 13 in the presence of 4.0 Å molecular sieves, yields an optically pure R-2-(5-bromo-6-methoxy-2-naphthyl)-hydroxy ethane (97%) in almost quantitative chemical yield. By following the route via nitrile with following oxidation to the corresponding carboxylic acid yields in 75% chemical yields a product of optically pure S-(+)-2-(5-bromo-6-methoxy-2-naphthyl) propionic acid, having a melting point mp 167° C.$[\alpha]_D^{20}$ +42.5° (c 0.6% in $CHCl_3$).

EXAMPLE 16

Preparation of R-(+)-1- (4-Isobutylphenyl) Hydroxyethane in the presence of Borohydride 10 g of (4S, 5S)-2-ethyl-4-hydroxymethyl-5-phenyl-2-oxazoline is dissolved in 100 ml of dry THF (0.05 mol) at 0° C. A solution of borane in THF (100 ml, 200 mmol), maintained under nitrogen, is added over 30 minutes to the solution of the oxazoline with efficient stirring in the presence of molecular sieves (4.0 Å, 1 g). After completion of the addition, the reaction mixture is stirred at 20°–25° C. for an additional 30 minutes. Through a dropping funnel, under $N_2$-atmosphere and at 20° C., 10.0 g C 5 mmol) 1-(4-[2-methylpropyl]-phenyl)-ethanone, which has been dissolved in 20 ml of dry THF, are being added dropwise under continuous stirring in the presence of molecular sieves (4.0 Å) by keeping the temperature at 20° C. over a period of 30 minutes. The oxazoline-organo-borane complex after reaction with the unsymmetrical ketone is treated with 10 ml of methanol, followed by 20.0 ml of 3M sodium-hydroxide maintaining the temperature at 30° C. of the reaction mixture. The reaction mixture ist further stirred for one hour, cooled (0° C.), and extacted with ether (3×100 ml). The extract is washed by successively with cold water (2×50 ml) and brine (3 ml), subsequently dried over magnesium sulphate. The organic layer is carefully fractionated to provide the chiral alcohol, b.p. 20.5° C./0.2 min Hg, yield 30%. $[\alpha]_D^{23}$ (neat), enantiomeric excess 98.1%

The recovery of the corresponding trans-(4S, 5S)-2-ethyl-4-hydroxymethyl-5-phenyl -2-oxazoline, having a melting point of 68.5° C., $[\alpha]_{580}^{22}$ −135,7° (C 11.0 in $CHCl_3$) was 75%.

EXAMPLE 17

Preparation of S-(+)-2-(4-Isobutylphenyl]Propionic Acid from the corresponding R-(+)-1-(-4 Isobutylphenyl)-Hydroxy-Ethane 10 g of R-(+)-1-[4-isobutylphenyl]-chloroethane (50,5 mmol), prepared from the R-(+)-2-(4-isobutyl-phenyl)-hydroxy-ethane by reacting $SOCl_2$ in dry pyridine, are dissolved in 25 ml EtOH and 15 ml water, and reacted with 2.95 g (60 mol) sodium cyanide, dissolved in 10 ml $H_2O$ under dropwise addition of the chloride solution unter continuous stirring. The mixture is refluxed for one hour and allowed to cool down to 20° C. The precipitated sodium chloride is filtered off and the supernatant, containing water and EtOH are dried and EtOH is distilled from the remaining liquid, which contains the S-(+)-1-[4-isobutyl phenyl]-ethyl cyanide (Chemical yield 88%). This S-(+) cyanide is dissolved in 15 ml EtOH and 30 ml water, which contains 9 g (0.45 mol) sodium hydroxide and 10% (w/w) $H_2O_2$ and heated under reflux conditions for one hour. After cooling to room temperature the reaction mixture is diluted with 100 ml water until a clear and transparent solution appears. This solutio is cooled down to 0° C. and 100 ml of diluted hydrochloric acid is subsequently added, when S-(+)-ibuprofen precipitates as small crystals. The S-(+)-ibuprofen crystals are collected, washed with dilute hydrochloric acid and dried over Ca $Cl_2$. The chemical yield is 94% and the melting point was 51°-54° C. $[\alpha]_D^{20}$ +60° (95%EtOH).

R-(+)-1-[4-isobutylphenyl]-chloroethane are obtained by reacting $SOCl_2$ in dry pyridine with 10 g of R-(+)-1-[4-isobutylphenyl]-hydroxy-ethane (56 mol at 20° C). Under continuous mixing of 6.7 g $SOCl_2$ (equivalent of 4.1 ml liquid $SOCl_2$) is added and refluxed for 20 minutes. After remaining the excess of $SOCl_2$ and pyridine (b.p. 116° C., 760 mm Hg) the chloride is distilled at 6 mm Hg (b.p. 23.3° C.) to yield 9.57 g of R-(+)-1-[4-isobutylphenyl]-chloroethane (36.6%).

EXAMPLE 18

10 ml R-(+)-2-3 isobutylphenyl-chlorethane (50.5 mmol) are dissolved in 150 ml of dimethyl formamide (DMF) (0.033M) under rapid mixing and $N_2$-stream, 10.8 g sodium-tetracarbonylferrate-II which is freshly prepared by treatment of iron-pentacarbonyl $Fe(CO)_5$ with sodium amalgan and THF at 20° C., are added by continuous mixing. The solution is cooled down to 10° C. and a stream of carbon monoxide is passed through the solution. Normally, the reaction is finished after 1-2 hours, depending on temperature and solvents (THF, DMF, DMSO); however, it can easily be monitored when an excess of carbon monoxide is leaving the solution in the presence of $N_2$. The oxidative cleavage to the corresponding S-(+)-2-[isobutyl phenyl] propionic acid is achieved by adding an aqueous solution of sodium hypochloride with subsequent addition of 0.1M hydrochloric acid by keeping the reaction temperature at 10° C. Care must be taken to add enough hydrochloric acid since most of the protons are used for precipitation of S-(+)-ibuprofen in aqueous solution for recovery of the free acid The corresponding amide from S-(+)-ibuprofen can be prepared by using triphenyl phosphine ($Ph_2P$) instead of carbon monoxide in the presence of sodium tetracarbonyl ferrate (II) ($Na_2Fe(CO_4)$). 10 g of R-(+)-2-[4-isobutyl phenyl]-chlorethane are dispered in 30 ml benzene in the presence of 10.8g sodium tetracarbonyl ferrate-(II) at 20° C. 13.4 g triphenyl phosphine (0.051 mol) dissolved in dry benzene are added dropwise during a period of time of 20 minutes under $N_2$ atmosphere. The mixture is refluxed under continuous stirring for three hours, the reaction mixture is left standing for one hour at 20° C. with subsequent quenching of the reaction with methyl-benzylamine. The samll crystalsof S-(+)-ibuprofen methyl benzylamide are filtered off, recrystallized from THF/DMF, are analyzed by HPLC-methods for opticl purity: the HPLC-analysis shows the presence of 98% diastereoisomer corresponding to S-2-(4-isobutyl phenyl) propionic acid at retention times of 2.79 minutes and 2% diastereiosomer corresponding to R-7-(4-isobutyl phenyl) propionic acid at retention times of 2.38 minutes. The chemical yields for producing the S-2-carboxylic acid from the corresponding R-(+)-[4-isobutyl phenyl]-chloroethane are, in the presence of carbon monoxide, almost 95% with an opticl purity of 95-98%, and 90% in the presene of triphenyl phosphine, respectively.

EXAMPLE 19

Several reductions of unsymmetrical ketones have been performed applying either reductions with Li Al $H_4$-oxazoline-complex and $BH_3$-oxazoline-complexes to the corresponding chiral hydroxy compounds. Table III and IV lists the reductions by (4S, 5S) 2-ethyl-4-hydroxymethyl-4-phenyl-2-oxazoline in the presence of either borane or lithium-aluminum, aluminum-hydride.

EXAMPLE 20

Preparation of R-(+)-2-(4-Isobutylphenyl) Hydroxyethane through reduction with (+) diisopinocampheylborane in complex with trans (4S, 5S)-2-ethyl-4-hydroymethyl-5- phenyl -2-oxazoline.

To a stirred solution (suspension) of diisopinocampheylborane (50 mmol) in THF (dry, 20 ml) is added 55 g (50 mmol) (4S, 5S)-2- ethyl -4-hydroxymethyl-5-phenyl-2-oxazoline in THF (dry, 30 ml). The reaction mixture ist stirred at 20° C. for five hours. The solid of diisopinocamphenylborne disappears and the formation of the complex is complete. To this complex solution 30.0 g. (40 mmol) of 1-(4-[2-methylpropyl]-phenyl]ethanone which has been dissolved in 50 ml of dry THF (or $CH_2$ $Cl_2$) are added dropwise under continuous mixing by keeping the temperature at 20° C. over a period of time of 30 minutes. The enantiomeric excess of the corresponding chirol alcohol can be enhanced to about 99% if the solution is being stirred in the presence of 2.0 g of molecular sieves (4.0 Å). The suspension yields a colourless solution after addition of the ketone which is left for completing the reaction for another 30 minutes in the presence of molecular sieves (4.0 Å).

The mixture is hydrolysed with 50.0 ml of water, after remaining the temperature to 25° C., diluhd with hydrochloric acid which is being added in order to save the chiral oxazoline for later use. The clear solution is entracted with $Et_2O$

EXAMPLE 21

Preparation of S-(+)-Ibuprofen

10ml (R-(+)-1-[4-isobutylphenyl]-chloroethane (50.5 mmol) are dissolved in 150 ml of dimethyl formamide (DMF)(0.033M) under rapid mixing and $N_2$-stream, 10.8 g sodium-tetracarbonyl-ferrate-II which is freshly prepared by treatment of iron-pentacarbonyl $Fe(CO)_5$ with sodium amalgam and THF at 20° C., are added by contiuous mixing. The solution is cooled down to 10° C. and a stream od carbon monoxide is passed through the solution. Normally, the reaction is finished after 1-2 hours, depending on temperature and solvents (THF, DMF, DMSO); however, it can easily be monitored when an excess of carbon monoxide is leaving the solution in the presence of $N_2$. The oxidative cleavage of the corresponding S-(+)-2-[isobutyl phenyl] propionic acid is achieved by adding an aqueous solution of sodium hypochloride with subsequent addition of 0.1M hydrochlorid acid by keeping the reaction temperature at 10° C. Care must be taken to add enough hydrochloric acid since most of the protons are used for precipitation of S-(+)-ibuprofen in aqueous solution for recovery of the free acid.

The corresponding amide from S-(+)-ibuprofen can be prepared by using triphenyl phosphine (Ph₃P) instead of carbon monoxide in the presence of sodium tetracarbonyl ferrate (II)(Na₂ Fe(CO₄)). 10 g of R-(+)-1-[4-isobutyl phenyl]-chlorethane are dispersed in 30 ml benzene in the presence of 10.8 g sodium tetracarbonyl ferrate-(II) at 20° C. 13.4 g triphenyl phosphine (0.051 mol) dissolved in dry benzene are added dropwise during a period of time of 20 minutes under N₂ atmosphere. The mixture is refluxed under continuous stirring for three hours, the reaction mixture is left standing for one hour at 20° C. with subsequent quenching of the reaction with methyl-benzylamide. The small crystals of S-(+)-ibuprofen methyl benzylamide are filtered off, recrystallized from THF/DMF, and analyzed by HPLC-methods for optical purity: the HPLC-analysis shows the presence of 98% diastereisomer corresponding to (S-2-(4-isobutyl phenyl) propionic acid at retention times of 2.79 minutes and 2% diastereisomer corresponding to R-2-(4 isobutyl phenyl) propionic acid at retention times of 2.38 minutes. The chemical yields for producing the S-2-carboxylic acid from the corresponding R-(+)-[4-isobutyl phenyl]-chlorethane are, in the presence of carbon monoxide, almost 95% with an optical purity of 95-98%, and 90% in the presence of triphenyl phosphine, respectively.

pressing the enantiomeric excess (ee) achieved can be followed by the equation $$ee = \frac{E^1 - E^2}{E^1 + E^2} \times 100$$

in which $E^1$ is the amount of the first chiral form of the secondary alcohol and $E^2$ is the amount of the second chiral form of the same alcohol. The extent of stereoselectivity (ee) is determined by NMR-methods by treating the chiral carbinol obtained with excess acid chloride from R-(+)-2-methoxy-2-trifluoro-methyl-phenyl-acetic acid in pyridine according to Dale et al. (J. A. Dale, D. C. Dull and H. S. Mosher, J. Org. Chem. 34, 2543, 1969). The signals of both the O-methyl and 2-methyl groups of the R, R-diastereomer from methyl-phenyl-carbinol appear at higher magnetic fields than those of the R, S-diastereoisomers. The peaks are separated easily by a T 60 instrument and relative peak heights are revealed to give a good approximation of the isomeric composition. Furthermore, the ¹¹F resonances for the 2-CF₃ group and 94.1 MHz can be applied also are readily integrated.

TABLE IV

| | STEREOSPECIFIC REDUCTION OF ASYMMETRIC KETONES BY THE BH₃-OXAZOLINE COMPLEX | | | |
|---|---|---|---|---|
| NO. | KETONE | BH₃ OXAZOLINE COMPLEX | CONFORMATION | % ee |
| 1 | Ph-Co-Me | THF, Toluene | R | 97 |
| 2 | 6-methoxy-2-naphthyl-CO-Me | THF, Et₂O, Benzene | R | 97-98 |
| 3 | 3-Phenoxy-CO-Me | THF, CH₂Cl₂, Zylene | R | 96 |
| 4 | 4-isobutyl-phenyl CO-Me | THF, 1,4-Dioxane, CH₂Cl₂ | R | 97 |
| 5 | 5-bromo-6-hyudroxy 2-naphthyl-CO-Me | THF, 1,4-Dioxane, Benzene | R | 95-98 |
| 6 | 2,4'-difluoro-4-diphenyl-CO-Me | THF, 1,4-dioxane, Et₂O | R | 97 |
| 7 | 2,2'-difluoro-4-diphenyl-CO-Me | THF, CH₂Cl₂, Et₂O | R | 95 |
| 8 | 5-fluoro-6-methoxy-2-naphthyl-CO-Me | THF, 1,4-dioxane, Et₂O | R | 97.5 |
| 9 | 4-methylphenyl-CO-Me | THF, 1,4-dioxane, CH₂Cl₂ | R | 97.5 |
| 10 | M-chlorophenyl-CO-Me | THF, 1,4-dioxane, benzene | R | 92.0 |

The above embodiments and examples are given to illustrate the scope and spirit of the instant invention.

TABLE III

| No. | Ketone | LiAlH₄-oxazoline-complex | conf. | % ee |
|---|---|---|---|---|
| 1 | Ph-CO-Me | in THF, Et₂O, benzene, toluene | R | 97 |
| 2 | p-isobutylphenyl-CO-Me | in CH₂Cl₂, Et₂O, benzene | R | 98.5 |
| 3 | 6-methoxy-2-naphthyl-CO-Me | in CH₂Cl₂/THF, Et₂O | R | 97.2 |
| 4 | 3-phenoxyphenyl-CO-Me | THF, CH₂Cl₂, Et₂, O benzene | R | 95.5 |
| 5 | 5-bromo-6-hydroxy 2-naphthyl-CO-Me | benzene, CH₂Cl₂, Et₂O | R | 97.3 |
| 6 | 2,4'-difluoro-methoxy-4-diphenyl-CO-Me | CH₂Cl₂/THF, toluene, 1,4-dioxane | R | 98.1 |
| 7 | p-methylphenyl-CO-Me | THF, Et₂O, benzene | R | 97.2 |
| 8 | m-chlorophenyl-CO-Me | Et₂O, 1,4-dioxane | R | 96.5 |

CO = carbonyl

The legend for Table III is the following: "ee" is the enantiomeric excess and conf. has the meaning of conformation, R or S enantiomer according to the Cahn-Prelog-rules.

The term "enantiomeric excess, ee" as applied herein refers to the increase in the amount of one enantiomer as compared to the other. A convenient method of ex- These embodiments and examples will make apparent, to those skilled in the art, other embodiments and examples. These other embodiments are within the contemplation of the present invention. Therefore, the present invention should be limited only by the appended claims.

What is claimed is:

1. A process for preparing a pharmaceutically active compound having the formula

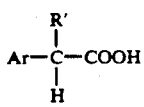

or pharmaceutically acceptable salts thereof wherein Ar is a monocyclic, polycyclic or orthocondensed polycyclic aromatic group having up to 14 carbon atoms in the aromatic ring and which may be unsubstituted or substituted in the aromatic ring which comprises
  (a) reacting 2-alkyl-4-alkoxy-5-phenyl-2-oxazoline with a Group I metal containing base wherein said oxazoline has the formula

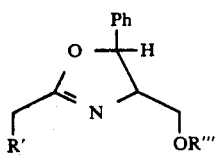

wherein
R' is lower alkyl;
R''' is alkyl containing 1-10 carbon atoms
Ph is phenyl or phenyl substituted with lower alkyl;
  (b) reacting the product thereof in (a) with Ar-Hal, wherein Ar is as defined hereinabove and Hal is halide.

2. The process according to claim 1 wherein Ar is unsubstituted or substituted with lower alkyl, lower alkoxy, aryloxy, lower aryloxy, aryl, hydroxy or halo.

3. The process according to claim 2 in which Ar is 4-isobutylphenyl, 6-methoxy-2-naphthyl, 3-phenoxyphenyl, 2-fluoro-4-diphenyl, 4'fluoro-4-diphenyl, 5-chloro-6-methoxy-2-naphthyl, 5-bromo-6-methoxy-2-naphthyl, 4-chlorophenyl, 4-difluoromethoxyphenyl, 6-hydroxy-2-naphthyl or 5-bromo-6-hydroxy-2-naphthyl.

4. The process according to claim 1 in which the Group I metal containing base is a lithium containing base is lithium diisopropylamide.

5. The process according to claim 1 in which the Group I metal containing base is a lithium containing base is lithium diisopropylamide 6. The process according to claim 1 in which R' is alkyl containing 1-4 carbon atoms.

7. The process according to claim 1 in which R''' is alkyl containing 1-8 carbon atoms.

8. The process according to claim 6 in which R' is methyl, ethyl, n-butyl or isobutyl.

9. The process according to claim 7 in which R''' is methyl, ethyl, n-butyl, isobutyl or n-octyl.

10. The process according to claim 1 in which Ph is phenyl

11. The process according to claim 1 in which an effective amount of molecular sieves are additionally present.

12. The process according to claim 11 in which the molecular sieves are 4 Å molecular sieves.

13. The process according to claim 1 in which the compound formed is ibuprofen or naproxen.

14. The process according to claim 11 in which the compound formed is ibuprofen or naproxen.

15. The process according to claim 1 in which the compound is prepared in stereospecific form.

16. The process according to claim 15 in which the compound is prepared in the S form.

17. A process for preparing a pharmaceutically active compound in stereospecific form having the formula

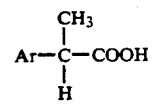

or pharmaceutically acceptable salts thereof wherein Ar is a monocyclic, polycyclic or orthocondensed polycyclic aromatic group having up to 14 carbons in the aromatic ring and which may be unsubstituted or substituted in the aromatic ring, which comprises
  (a) reacting (4S,5S)-2-alkyl-4-alkoxy-5-phenyl-2-oxazoline with a lithium containing base wherein said oxazoline has the formula:

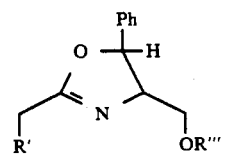

wherein
R' is lower alkyl
R''' is alkyl containing 1-10 carbon atoms
Ph is phenyl or phenyl substituted with lower alkyl
with a Group I metal containing base and
  (b) reacting the product thereof in (a) with Ar-Hal, wherein Ar is defined hereinabove and Hal is halide.

18. The process according to claim 17 wherein Ar is unsubstituted or substituted with lower alkyl, lower alkoxy, aryloxy, lower aryloxy, aryl, hydroxy or halo.

19. The process according to claim 18 in which Ar is 4-isobutylphenyl, 6-methoxy 2-naphthyl, 3-phenoxyphenyl, 2-fluoro-4-diphenyl, 2',4'-difluoro-4-diphenyl, 5-fluoro-6-hydroxy-2-naphthyl, 5-fluoro-6-methoxy-2-naphthyl, 2,2-difluoro-4-diphenyl, 5-chloro-6-methoxy-2-naphthyl, 5-bromo-6-methoxy-2-naphthyl, 4-chlorophenyl, 4-difluoromethoxyphenyl, 6-hydroxy-2-naphthyl or 5-bromo-6-hydroxy-2-naphthyl.

20. The process according to claim 17 in which the lithium containing base is lithium diisopropylamide.

21. The process according to claim 17 in which R' is alkyl containing 1-4 carbon atoms.

22. The process according to claim 17 in which R''' is alkyl containing 1-8 carbon atoms.

23. The process according to claim 21 in which R' is methyl, ethyl, n-butyl or isobutyl.

24. The process according to claim 22 in which R''' is methyl, ethyl, n butyl, isobutyl or n-octyl.

25. The process according to claim 17 in which an effective amount of molecular sieves are additionally present.

26. The process according to claim 25 in which the molecular sieves are 4 Å molecular sieves.

27. The process according to claim 17 in which the compound formed is S-ibuprofen or S-naproxen.

28. The according to claim 26 in which the compound formed is S-ibuprofen or S-naproxen.

29. The process according to claim 17 in which the 2-alkyl-4-alkoxy-5-phenyl oxazoline is prepared by reacting lower alkyl ortho lower alkanoate of the formula

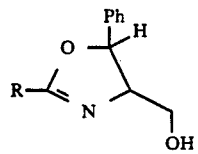

with (1S, 2S)-(+)-2-amino-1-phenyl-1,3-diol in the presence of an alkyl halide of the formula R'''X wherein R'' is lower alkyl.

30. The process according to claim 15 in which Ph is phenyl.

31. The process according to claim 1 wherein an acid is additionally present in step (b).

32. The process according to claim 31 wherein an acid is hydrochloric acid, sulfuric acid or nitric acid.

33. The process according to claim 17 wherein an acid is additionally present in step (b).

34. The process according to claim 33 wherein an acid is hydrochloric acid, sulfuric acid or nitric acid.

35. The process according to claim 1 wherein the Group I metal containing base is lithium lower alkylamide, lithium lower alkoxide, lithium acetylide, lithium hydride, lithium hydroxide or lithium triarylmethide.

36. The process according to claim 35 wherein the Group I metal containing base is lithium isopropylamide, lithium methoxide, lithium hydride, lithium acetylide, lithium hydroxide or lithium triphenylmethide.

37. The process according to claim 17 wherein the Group I metal containing base is lithium lower alkylamide, lithium lower alkoxide, lithium acetylide, lithium hydride, lithium hydroxide or lithium triarylmethide.

38. The process according to claim 35 wherein the Group I metal containing base is lithium isopropylamide, lithium methoxide, lithium hydride, lithium acetylide, lithium hydroxide or lithium triphenylmethide.

39. The process according to claim 1 wherein the Group I metal containing base is a lithium containing base.

40. The process according to claim 17 wherein the Group I metal containing base is lithium isopropylamide, lithium methoxide, lithium hydride, lithium acetylide, lithium hydroxide or lithium triphenylmethide.

41. The process according to claim 1 wherein the Group I metal containing base has a conjugate acid having a pKa greater than or equal to 15.

42. The process according to claim 17 wherein the Group I metal containing base has a conjugate acid having a pKa greater than or equal to 15.

* * * * *

UNITED STATES PATENT AND TRADEMARK OFFICE
CERTIFICATE OF CORRECTION

PATENT NO. : 5,248,815
DATED : September 28, 1993
INVENTOR(S) : H. Henrich Paradies It is certified that error appears in the above-indentified patent and that said Letters Patent is hereby corrected as shown below:

On the Title Page, under "OTHER PUBLICATIONS", Column 2, line 28, insert the following:

--Meyers, et al., Asymmetric Carbon-Carbon Bond Forming Reactions via Chiral Oxazolines, Asymmetric Reactions and processes in Chemistry, pages 83-98.

Collman, et al., Principles and Applications of Organotransition Metal Chemistry, Applications of Transition-Metal Carbonyl Compounds, pages 755-759.

Foulkes, et al., A simple Laboratory Procedure for the Preparation of Nitriles From Alcohols Via Unstable Chlorides in Large Quantitites, Synthetic Communications, 9(7), 625-630 (1979).

Rieu, et al., Methods for the Synthesis of Antiinflammatory 2-Aryl Propionic Acids, Tetrahedron Report Number 205.--

Column 4, line 57: "(Ph$_3$P)" should read --(PPh$_3$)--
     Column 6, line 56: "eLhyl" should read --ethyl--

UNITED STATES PATENT AND TRADEMARK OFFICE
CERTIFICATE OF CORRECTION

PATENT NO. : 5,248,815
DATED : September 28, 1993
INVENTOR(S) : H. Henrich Paradies It is certified that error appears in the above-indentified patent and that said Letters Patent is hereby corrected as shown below:

Column 8, lines 27-34: " 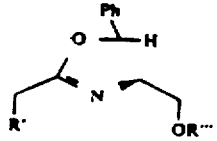 "

should read -- 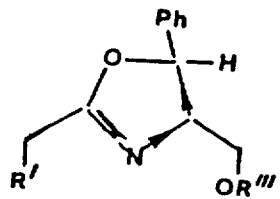 --

Column 8, lines 37-44: " 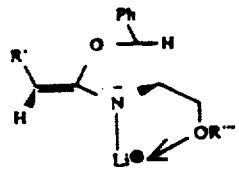 "

should read -- 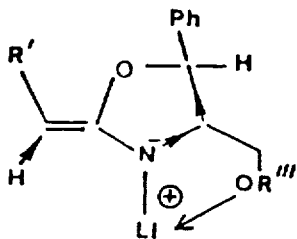 --

UNITED STATES PATENT AND TRADEMARK OFFICE
CERTIFICATE OF CORRECTION

Page 3 of 13

PATENT NO. : 5,248,815
DATED : September 28, 1993
INVENTOR(S) : H. Henrich Paradies It is certified that error appears in the above-indentified patent and that said Letters Patent is hereby corrected as shown below:

Column 9, lines 38-46:

" 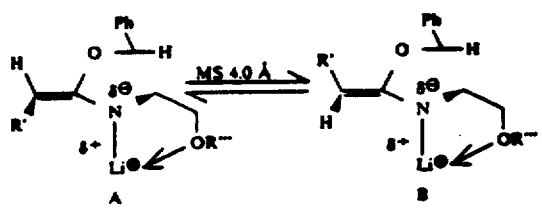 "

should read

-- 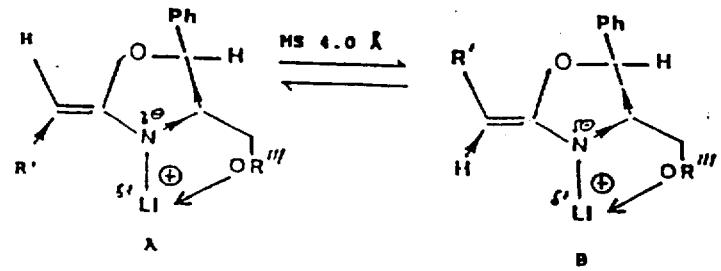 --

UNITED STATES PATENT AND TRADEMARK OFFICE
CERTIFICATE OF CORRECTION

PATENT NO. : 5,248,815
DATED : September 28, 1993
INVENTOR(S) : H. Henrich Paradies It is certified that error appears in the above-indentified patent and that said Letters Patent is hereby corrected as shown below:

Column 13, lines 24-29: " 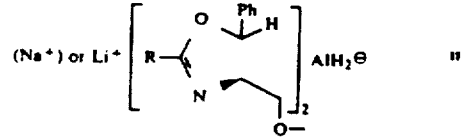 "

should read -- 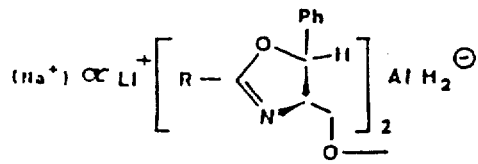 --

Column 15, lines 5-35: " 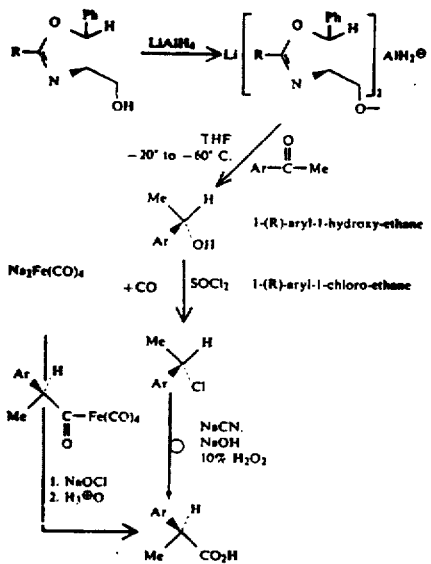 "

UNITED STATES PATENT AND TRADEMARK OFFICE
CERTIFICATE OF CORRECTION

PATENT NO. : 5,248,815
DATED : September 28, 1993
INVENTOR(S) : H. Henrich Paradies It is certified that error appears in the above-indentified patent and that said Letters Patent is hereby corrected as shown below:

should read

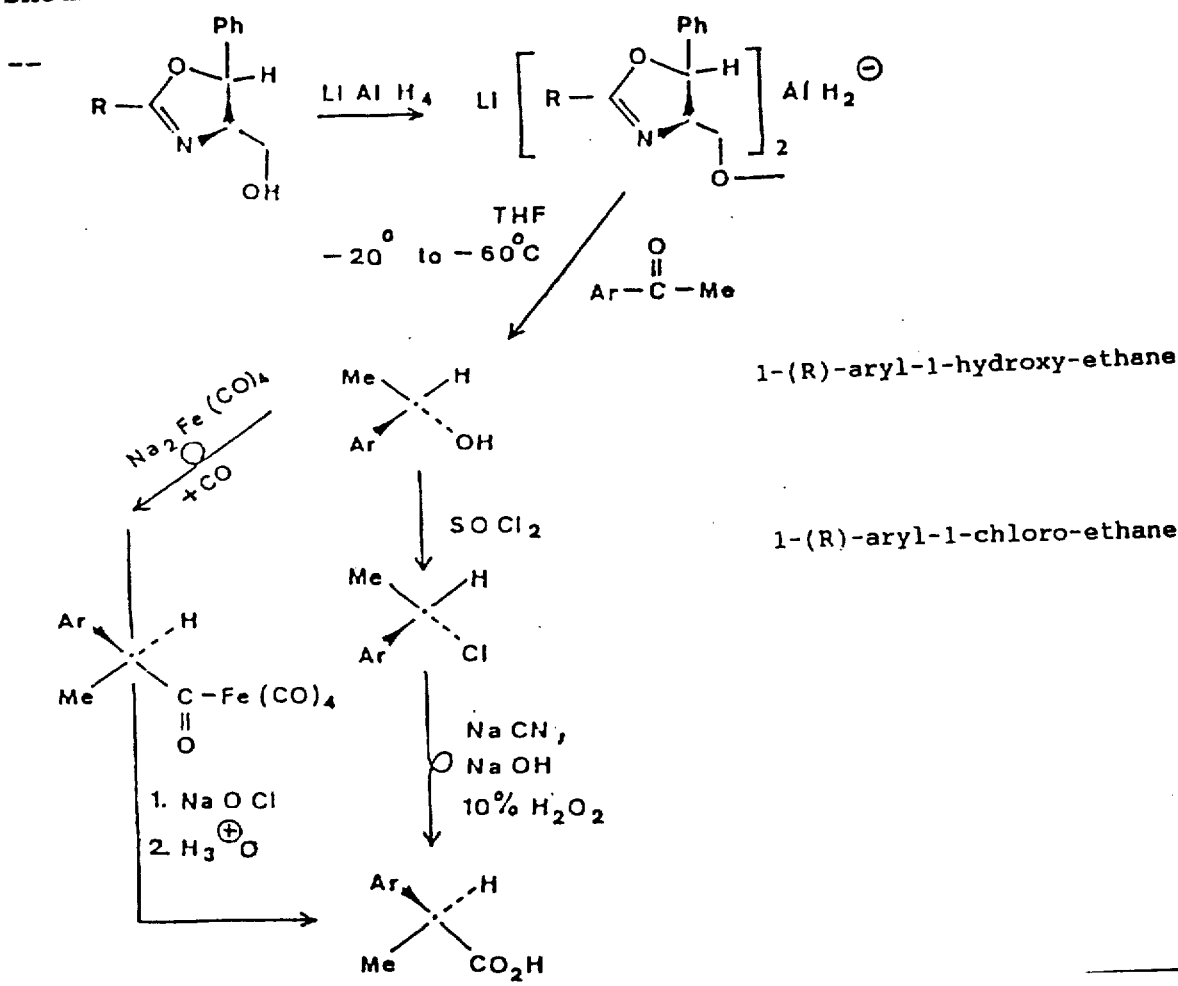

1-(R)-aryl-1-hydroxy-ethane 1-(R)-aryl-1-chloro-ethane

UNITED STATES PATENT AND TRADEMARK OFFICE
CERTIFICATE OF CORRECTION

Page 6 of 13

PATENT NO. : 5,248,815
DATED : September 28, 1993
INVENTOR(S) : H. Henrich Paradies It is certified that error appears in the above-indentified patent and that said Letters Patent is hereby corrected as shown below:

Column 15, lines 66-67: "$N_a2Fe(CO_4)$" should read --$Na_2Fe(CO)_4$--

Column 17, lines 36-49: "

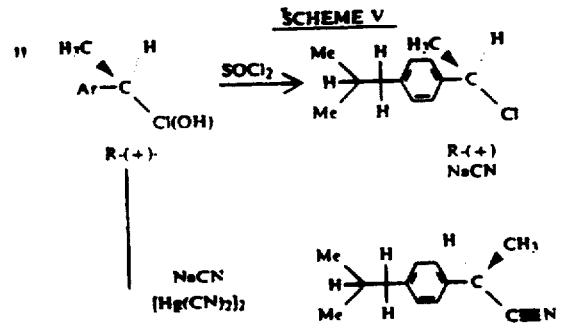

should read --

SCHEME V

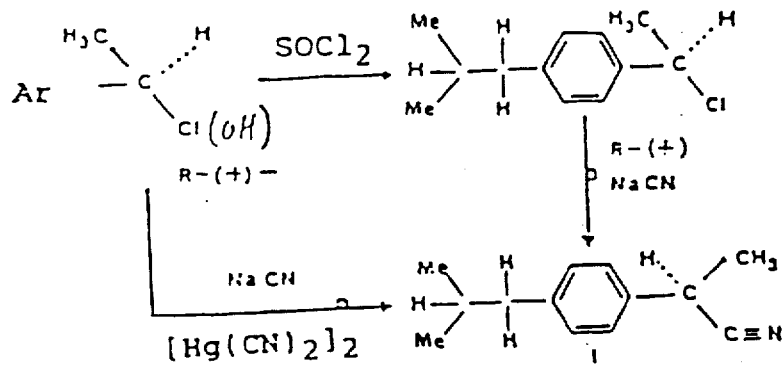

--

UNITED STATES PATENT AND TRADEMARK OFFICE
CERTIFICATE OF CORRECTION

PATENT NO. : 5,248,815
DATED : September 28, 1993
INVENTOR(S) : H. Henrich Paradies It is certified that error appears in the above-indentified patent and that said Letters Patent is hereby corrected as shown below:

Column 18, lines 51-56: " 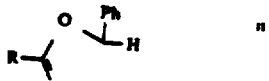 "

should read -- 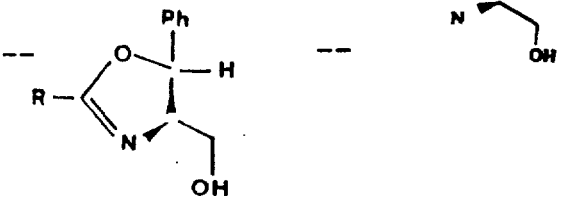 --

Column 20, lines 10-19:

" 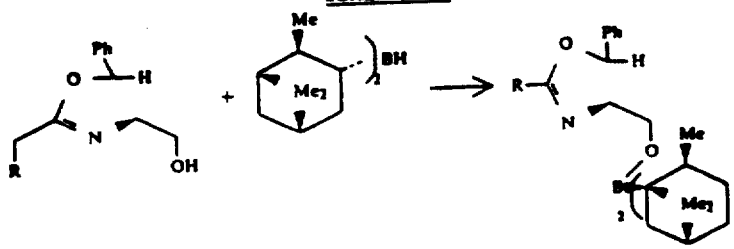 "

should read -- 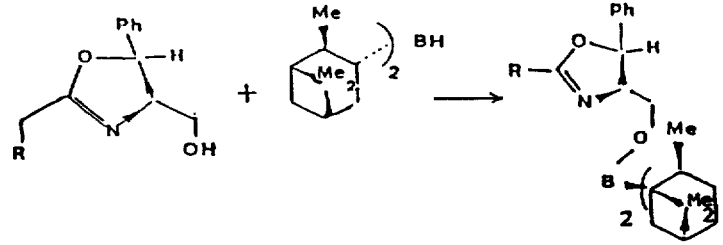 --

UNITED STATES PATENT AND TRADEMARK OFFICE
CERTIFICATE OF CORRECTION

PATENT NO. : 5,248,815
DATED : September 28, 1993
INVENTOR(S) : H. Henrich Paradies It is certified that error appears in the above-indentified patent and that said Letters Patent is hereby corrected as shown below:

Column 21, lines 36-37: "4isobutylphenyliode" should read --4-isobutylphenyliode--

Column 22, line 50: "$Na_2So_4$" should read --$Na_2SO_4$--

Column 22, line 52: "$[\alpha]589^{24}$" should read --$[\alpha]_{589}$--

Column 22, line 54: "fo" should read --for--

Column 23, line 23: "$[\alpha]_{589}^{24}$" should read --$[\alpha]_{589}$--

Column 23, line 35: "152°153°" should read --152° - 153°--

Column 23, lines 36-37: "$[\alpha]_D^{25} + 65\ 0°\ C$" should read --$[\alpha]^{25} + 65.0°C$--

Column 23, line 50: "both A" should read --bath. A--

Column 23, line 66: "$[\alpha]_{589}^{24}$" should read --$[\alpha]_{589}$--

Column 24, line 9: "[c" should read --(c--

Column 24, line 17: "both" should read --bath--

UNITED STATES PATENT AND TRADEMARK OFFICE
CERTIFICATE OF CORRECTION

Page 9 of 13

PATENT NO. : 5,248,815
DATED : September 28, 1993
INVENTOR(S) : H. Henrich Paradies It is certified that error appears in the above-indentified patent and that said Letters Patent is hereby corrected as shown below:

Column 24, lines 33 & 34: "$[\alpha]_{589}^{24}$" should read --$[\alpha]_{589}$--

Column 25, lines 1-2: "$[\alpha]_{589}^{24}$ -3.15°60 C" should read --$[\alpha]_{589}$ -31.5° C--

Column 25, lines 9 & 11: "$[\alpha]_{D}^{24}$" should read --$[\alpha]^{24}$--

Column 25, line 22: "A" should read --Å--

Column 25, line 24: delete second occurrnce of "of"

Column 25, lines 33 & 45: "$[\alpha]_{589}^{24}$" should read --$[\alpha]_{589}$--

Column 25, line 33: after ")" insert --.--

Column 26, line 3: "$[\alpha]_{589}^{24}$" should read --$[\alpha]_{589}$--

Column 26, line 3: after "$CHCl_3$" insert --)--

Column 26, line 9: "extracct" should read --extract--

Column 26, line 14: "$[\alpha]_{589}^{25}$" should read --$[\alpha]_{589}$--

Column 26, line 58: "$[\alpha]_{590}^{22}$" should read --$[\alpha]_{590}$--

UNITED STATES PATENT AND TRADEMARK OFFICE
CERTIFICATE OF CORRECTION

PATENT NO. : 5,248,815
DATED : September 28, 1993
INVENTOR(S) : H. Henrich Paradies It is certified that error appears in the above-indentified patent and that said Letters Patent is hereby corrected as shown below:

Column 27, line 8: "wit" should read --with--
Column 27, line 38: "$[\alpha]_D^{25}$" should read --$[\alpha]^{25}$--
Column 27, line 39: delete "or Altrnatively through"
Column 27, line 50: "containg" should read --containing--
Column 27, line 67: "$[\alpha]_D^{20}$" should read --$[\alpha]^{20}$--
Column 28, line 16: "$[\alpha]_D^{20}$" should read --$[\alpha]^{20}$--
Column 28, line 41: "ist" should read --is--
Column 28, line 47: "$[\alpha]_D^{23}$" should read --$[\alpha]^{23}$--
Column 28, line 51: "$[\alpha]_{580}^{22}$" should read --$[\alpha]_{580}$--
Column 28, line 55: "]" should read --)--
Column 29, line 9: "solutio" should read --solution--
Column 29, line 15: "$[\alpha]_D^{20}$" should read --$[\alpha]^{20}$--
Column 29, lines 27 & 52: "chlorethane" should read --chloroethane--
Column 29, line 47: after "acid" insert --.--

UNITED STATES PATENT AND TRADEMARK OFFICE
CERTIFICATE OF CORRECTION

PATENT NO. : 5,248,815
DATED : September 28, 1993
INVENTOR(S) : H. Henrich Paradies It is certified that error appears in the above-indentified patent and that said Letters Patent is hereby corrected as shown below:

Column 29, line 52: "dispered" should read --dispersed--

Column 29, line 60: "samll crystalsof" should read --small crystals of--

Column 29, line 63: "opticl" should read --optical--

Column 30, line 4: "opticl" should read --optical--

Column 30, line 4: "presene" should read --presence--

Column 30, line 20: "hydroymethyl" should read --hydroxymethyl--

Column 30, line 25: "ist" should read --is--

Column 30, line 28: "phenyl]" should read --phenyl)--

Column 30, line 33: "chirol" should read --chiral--

Column 30, line 39: "hydrolysed" should read --hydrolyzed--

Column 30, line 40: "dilhud" should read --diluted--

Column 30, line 43: after "Et$_2$O" insert --.--

Column 30, line 55: "od" should read --of--

UNITED STATES PATENT AND TRADEMARK OFFICE
CERTIFICATE OF CORRECTION

PATENT NO. : 5,248,815
DATED : September 28, 1993
INVENTOR(S) : H. Henrich Paradies It is certified that error appears in the above-indentified patent and that said Letters Patent is hereby corrected as shown below:

Column 30, lines 64 & 65: "hydrochlorid" should read --hydrochloric--

Column 31, lines 5 & 23: "chlorethane" should read --chloroethane--

Column 31, line 30, Table IV: "Ph-Co-Me" should read --Ph-CO-Me--

Column 31, line 36, Table IV: "hyudroxy" should read --hydroxy--

Column 31, line 55, Table III: "$Et_2$," should read --$Et_2$),--

Column 32, line 16: "R-diastereomer" should read --R-diastereoisomer--

Column 32, line 17: "fiels" should read --fields--

Column 33, line 47, Claim 4: after "base" insert --and--

Column 33, lines 45-51: delete Claim 5

Column 33, line 60, Claim 10: after "phenyl" insert --.--

UNITED STATES PATENT AND TRADEMARK OFFICE
CERTIFICATE OF CORRECTION

PATENT NO. : 5,248,815
DATED : September 28, 1993
INVENTOR(S) : H. Henrich Paradies It is certified that error appears in the above-indentified patent and that said Letters Patent is hereby corrected as shown below:

Column 34, line 61, Claim 24: "n butyl" should read --n-butyl--

Column 35, line 1, Claim 28: after "The" insert --process--

Signed and Sealed this

Twenty-sixth Day of November 1996

BRUCE LEHMAN

Attest:

Attesting Officer

Commissioner of Patents and Trademarks